(12) United States Patent
Harriman et al.

(10) Patent No.: US 10,687,519 B2
(45) Date of Patent: *Jun. 23, 2020

(54) TRANSGENIC ANIMAL FOR PRODUCTION OF ANTIBODIES HAVING MINIMAL CDRS

(71) Applicant: Crystal Bioscience Inc., San Diego, CA (US)

(72) Inventors: William Don Harriman, Alameda, CA (US); Robert Etches, Oakland, CA (US); Philip A. Leighton, San Francisco, CA (US)

(73) Assignee: CRYSTAL BIOSCIENCE INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/428,763

(22) Filed: May 31, 2019

(65) Prior Publication Data

US 2019/0320630 A1 Oct. 24, 2019

Related U.S. Application Data

(60) Continuation of application No. 16/209,807, filed on Dec. 4, 2018, now Pat. No. 10,362,770, which is a continuation of application No. 15/996,373, filed on Jun. 1, 2018, now Pat. No. 10,172,334, which is a continuation of application No. 15/377,940, filed on Dec. 13, 2016, now Pat. No. 10,010,058, which is a continuation of application No. 15/188,724, filed on Jun. 21, 2016, now Pat. No. 9,549,538, which is a division of application No. 14/057,820, filed on Oct. 18, 2013, now Pat. No. 9,404,125, which is a division of application No. 12/854,722, filed on Aug. 11, 2010, now Pat. No. 8,592,644.

(60) Provisional application No. 61/274,319, filed on Aug. 13, 2009.

(51) Int. Cl.
| | | |
|---|---|---|
| *A01K 67/00* | (2006.01) | |
| *A01K 67/027* | (2006.01) | |
| *C07K 16/00* | (2006.01) | |
| *C12N 15/85* | (2006.01) | |
| *C12N 15/87* | (2006.01) | |
| *C12P 21/02* | (2006.01) | |

(52) U.S. Cl.
CPC ...... *A01K 67/0275* (2013.01); *A01K 67/0278* (2013.01); *C07K 16/00* (2013.01); *C12N 15/8509* (2013.01); *C12N 15/87* (2013.01); *C12P 21/02* (2013.01); *A01K 2207/15* (2013.01); *A01K 2217/05* (2013.01); *A01K 2217/072* (2013.01); *A01K 2227/30* (2013.01); *A01K 2267/01* (2013.01); *C07K 2317/14* (2013.01); *C07K 2317/21* (2013.01); *C07K 2317/24* (2013.01); *C07K 2317/565* (2013.01); *C07K 2317/567* (2013.01); *C12N 2015/8518* (2013.01); *C12N 2517/02* (2013.01)

(58) Field of Classification Search
CPC .................. A01K 67/0275; A01K 67/0278
See application file for complete search history.

(56) References Cited

U.S. PATENT DOCUMENTS

| | | | |
|---|---|---|---|
| 5,545,806 | A | 8/1996 | Longberg et al. |
| 5,545,807 | A | 8/1996 | Surani et al. |
| 5,625,126 | A | 4/1997 | Longberg et al. |
| 5,633,426 | A | 5/1997 | Namikawa et al. |
| 5,759,763 | A | 6/1998 | Naito et al. |
| 6,333,192 | B1 | 12/2001 | Petitte et al. |
| 6,461,864 | B1 | 10/2002 | Soriano et al. |
| 6,512,161 | B1 | 1/2003 | Rouy et al. |
| 6,673,986 | B1 | 1/2004 | Kucherlapati et al. |
| 6,861,572 | B1 | 3/2005 | Etches et al. |
| 6,872,569 | B2 | 3/2005 | Lee et al. |
| 7,041,870 | B2 | 5/2006 | Tomizuka et al. |
| 7,049,426 | B2 | 5/2006 | Green et al. |
| 7,064,244 | B2 | 6/2006 | Jakobovits et al. |
| 7,129,084 | B2 | 10/2006 | Buelow et al. |
| 7,145,057 | B2 | 12/2006 | Van De et al. |
| 7,249,569 | B2 | 7/2007 | Mendu et al. |
| 7,323,618 | B2 | 1/2008 | Zhu et al. |

(Continued)

FOREIGN PATENT DOCUMENTS

| | | |
|---|---|---|
| WO | WO2002012437 | 2/2002 |
| WO | WO2005007696 | 1/2005 |

(Continued)

OTHER PUBLICATIONS

Birtalan, et al. "The functional capacity of the natural amino acids for molecular recognition", Mol Biosyst., 7:1186-94, 2010.

(Continued)

*Primary Examiner* — Marcia S Noble
(74) *Attorney, Agent, or Firm* — James S. Keddie; Bozicevic, Field & Francis LLP

(57) ABSTRACT

A transgenic animal is provided. In certain embodiments, the transgenic animal comprises a genome comprising: an immunoglobulin light chain locus comprising: a) a functional immunoglobulin light chain gene comprising a transcribed variable region encoding: i. light chain CDR1, CDR2 and CDR3 regions that are composed of 2 to 5 different amino acids; and ii. a light chain framework; and, operably linked to the functional immunoglobulin light chain gene: b) a plurality of pseudogene light chain variable regions each encoding: i. light chain CDR1, CDR2 and CDR3 regions that are composed of the same 2 to 5 different amino acids as the CDRs of the functional gene; and ii. a light chain framework that is identical in amino acid sequence to the light chain framework of the transcribed variable region.

15 Claims, 12 Drawing Sheets

Specification includes a Sequence Listing.

(56) References Cited

U.S. PATENT DOCUMENTS

| | | |
|---|---|---|
| 7,323,619 B2 | 1/2008 | Baltimore et al. |
| 7,476,776 B2 | 1/2009 | Han et al. |
| 7,585,668 B2 | 9/2009 | Buelow et al. |
| 2002/0028488 A1 | 3/2002 | Singh et al. |
| 2002/0108132 A1 | 8/2002 | Rapp |
| 2002/0114790 A1 | 8/2002 | Neiman |
| 2002/0138864 A1 | 9/2002 | Han et al. |
| 2002/0162134 A1 | 10/2002 | Baguisi et al. |
| 2003/0061629 A1 | 3/2003 | Sutrave |
| 2003/0170888 A1 | 9/2003 | Van De et al. |
| 2003/0172387 A1 | 9/2003 | Zhu et al. |
| 2003/0182675 A1 | 9/2003 | Etches et al. |
| 2004/0226058 A1 | 11/2004 | deLeon et al. |
| 2005/0114916 A1 | 5/2005 | Etches et al. |
| 2005/0246782 A1 | 11/2005 | Etches et al. |
| 2005/0282273 A1 | 12/2005 | Swiatek, II |
| 2006/0026696 A1 | 2/2006 | Buelow et al. |
| 2006/0053504 A1 | 3/2006 | Zhu et al. |
| 2006/0110824 A1 | 5/2006 | Chen et al. |
| 2006/0174362 A1 | 8/2006 | Van de Lavoir et al. |
| 2006/0174363 A1 | 8/2006 | Van de Lavoir et al. |
| 2006/0183195 A1 | 8/2006 | Longberg et al. |
| 2006/0191026 A1 | 8/2006 | Zhu et al. |
| 2006/0206952 A1 | 9/2006 | Van de Lavoir et al. |
| 2007/0092505 A1 | 4/2007 | Buelow et al. |
| 2007/0196376 A1 | 8/2007 | Raeber et al. |
| 2009/0060908 A1 | 3/2009 | Cardarelli et al. |
| 2009/0083871 A1 | 3/2009 | Etches et al. |
| 2009/0083872 A1 | 3/2009 | Etches et al. |
| 2009/0165155 A1 | 6/2009 | Zhu et al. |
| 2010/0138946 A1 | 6/2010 | Van de Lavoir et al. |
| 2010/0192241 A1 | 7/2010 | Etches et al. |
| 2011/0023160 A1 | 1/2011 | Etches et al. |
| 2011/0028696 A1 | 2/2011 | Cardarelli et al. |
| 2011/0055938 A1 | 3/2011 | Harriman et al. |
| 2011/0179510 A1 | 7/2011 | Van de Lavoir et al. |
| 2011/0277048 A1 | 11/2011 | Etches et al. |
| 2011/0296541 A1 | 12/2011 | Etches et al. |

FOREIGN PATENT DOCUMENTS

| | | |
|---|---|---|
| WO | WO2005012359 | 2/2005 |
| WO | WO2005012531 | 2/2005 |
| WO | WO2007064919 | 6/2007 |
| WO | WO2007094842 | 8/2007 |
| WO | WO2012162422 | 11/2012 |
| WO | WO2013059159 | 4/2013 |

OTHER PUBLICATIONS

Delavoir, et al. "Germline transmission of genetically modified primordial germ cells", Nature, 441:766-9, 2006.

Fellouse, et al., "High-throughput generation of synthetic antibodies from highly functional minimalist phage-displayed libraries", J Mol Biol., 4:924-40, 2007.

Fukagawa, et al., "The chicken HPRT gene: a counter selectable marker for the DT40 cell line", Nucleic Acids Research, 27:1966-1969, 1999.

Ishida, et al., "Production of human monoclonal and polyclonal antibodies in TransChromo animals", Cloning Stem Cells., 4:91-102, 2002.

Ivarie, et al,., "Avian transgenesis: progress towards the promise", Trends in biotechnology, 21:14-9, 2003.

Kanayama, et a., "Genetic manipulation of an exogenous non-immunoglobulin protein by gene conversion machinery in a chicken B cell line", Nucleic Acids Res, 34, 2004.

Kiode, et al., "The Importance of Being Tyrosine: Lessons in Molecular Recognition from Minimalist Synthetic Binding Proteins", ACS Chem. Biol., 4:325-34, 2009.

Leighton, et al., "Genetic modification of primordial germ cells by gene trapping, gene targeting, and phiC31 integrase", Mol Reprod Dev., 7:1163-75, 2008.

Li, et al. "Recent progress on technologies and applications of transgenic poultry", African Journal of Biotechnology, 94:3481-3488, 2010.

Longberg, et al., "Human antibodies from transgenic animals", Nat Biotechnol., 9:1117-25, 2005.

Love, et al., "Transgenic birds by DNA microinjection", Biotechnology, 1:60-3, 1994.

Mohammed, et al., "Deposition of genetically engineered human antibodies into the egg yolk of hens", Immunotechnology., 4:115-25,1998.

Pain, et al., "Long-term in vitro culture and characterisation of avian embryonic stem cells with multiple morphogenetic potentialities", Development., 8:2339-48, 1996.

Priddle, et al., "New frontiers in gene targeting and cloning: success, application and challenges in domestic animals and human embryonic stem cells", Reproduction., 1:1-11, 2003.

Reynaud, et al., "Somatic hyperconversion diversifies the single Vh gene of the chicken with a high incidence in the D region", Cell., 1:171-83, 1989.

Sayegh, et al., "Avian B cell development: lessons from transgenic models", Vet Immunol Immunopathol., 72:31-7, 1999.

Thoroval, et al., "Germline transmission of exogenous genes in chickens using helper-free ecotropic avian leukosis virus-based vectors",Transgenic Research 4:369-376, 1995.

Vick, et al., "Transgenic birds from transformed primordial germ cells", Proc. Soc. Lond., 251:179-182, 1993.

Yang, et. al., "Control of gene conversion and somatic hypermutation by immunoglobulin promoter and enhancer sequences", J Exp Med., 203:2919-28, 2006.

Yelamos, et al., Targeting of non-Ig sequences in place of the V segment by somatic hypermutation Nature, 376;225-229, 1995.

Arakawa, et al., "Immunoglobulin Gene Conversion: Insights From Bursal B Cells and the DT40 Cell Line", Developmental Dynamics, 229:458-464, 2004.

Buelow, et al., "Expression of a humanized antibody repertoire in transgenic rabbits", Human Antibodies, 15:19-23, 2006.

Courtenay-Luck, Nigel, "Session 5: Molecular Biology II", Human Antibodies 15, (2006), 19-28.

Fellhouse, et al., "Molecular recognition by a binary code", J Mol Biol.;348(5):1153-62, 2005.

Fellhouse, et al., "Synthetic antibodies from a four-amino-acid code: a dominant role for tyrosine in antigen recognition", Proc Natl Acad Sci U S A.,101(34):12467-72, 2004.

Fellhouse, et al., "Tyrosine plays a dominant functional role in the paratope of a synthetic antibody derived from a four amino acid code", J Mol Biol.,357(1):100-14, 2006.

Hoet, et al., "Generation of high-affinity human antibodies by combining donor-derived and synthetic complementarity-determining-region diversity", Nat Biotechnol., 23(3):344-8, 2005.

Ratcliffe, et al., "Antibodies, immunoglobulin genes and the bursa of Fabricius in chicken B cell development", Developmental & Comparative Immunology, vol. 30, Issues 1-2, pp. 101-118, 2006.

Seo, et al., "Rapid generation of specific antibodies by enhanced homologous recombination", Nature Biotechnology, 23, 731-735, 2005.

Koide, et al., "The Importance of Being Tyrosine: Lessons in Molecular Recognition from Minimalist Synthetic Binding Proteins", ACS Chem Biol., 4(5): 325-334, 2009.

Sidhu, et al., "Phage-displayed antibody libraries of synthetic heavy chain complementarity determining regions", J Mol Biol., 338(2):299-310, 2004.

Schusser, et al., "Immunoglobulin knockout chickens via efficient homologous recombination in primordial germ cells", Proc Natl Acad Sci U S A., 110(50):20170-5, 2013.

Schusser, et al., "Harnessing Gene Conversion in Chicken B Cells to Create a Human Antibody Sequence Repertoire", PLoS ONE, vol. 8, issue 11, p. e80108, 2013.

| | Vk:F4 | Vk:H12 | Vk:D10 | Vk:F5 | Vk:B3 | Vk:E1 | Vk:D12 | Vk:C7 | Sum |
|---|---|---|---|---|---|---|---|---|---|
| VH:225 E9 | 25.0 | 17.5 | 24.0 | 26.0 | 27.8 | 24.8 | 25.7 | 25.4 | 196.2 |
| VH:225 C6 | 25.2 | 19.1 | 25.3 | 26.4 | 26.3 | 26.8 | 26.0 | 29.0 | 204.1 |
| VH:225 E11 | 23.5 | 18.3 | 23.9 | 25.2 | 26.3 | 27.3 | 26.6 | 25.6 | 196.8 |
| VH:225 E3 | 26.9 | 18.2 | 26.6 | 28.8 | 28.0 | 26.6 | 24.7 | 27.9 | 207.6 |
| VH:225 G8 | 24.9 | 17.6 | 25.5 | 27.9 | 28.7 | 28.1 | 23.9 | 27.5 | 204.2 |
| VH:225 C4 | 25.3 | 17.3 | 24.6 | 25.3 | 25.9 | 23.4 | 19.6 | 24.8 | 186.3 |
| VH:225 D3 | 25.3 | 16.2 | 24.2 | 24.9 | 25.3 | 19.9 | 13.9 | 24.6 | 174.2 |
| VH:225 D1 | 28.6 | 21.1 | 28.1 | 28.4 | *29.4 | 27.5 | 24.7 | 27.5 | 215.2 |
| Sum | 204.9 | 145.4 | 202.1 | 212.9 | 217.7 | 204.3 | 185.1 | 212.3 | |

*best HxL pair of matrix

Fig. 9

SEQUENCE LISTING

```
<160> NUMBER OF SEQ ID NOS: 43

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucelotide

<400> SEQUENCE: 1
cagagttaac gcagcaac                                                   18

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Gln Ser Val Ser Ser Asn
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Tyr Ser Ser Tyr Ser Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Ser Tyr Ser Ser Tyr Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ser Ser Tyr Ser Ser Tyr
1               5

<210> SEQ ID NO 6
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 6

Tyr Ser Tyr Ser Tyr Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Ser Tyr Ser Tyr Ser Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Tyr Ser Ser Ser Ser Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Tyr Tyr Ser Ser Ser Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Ser Tyr Tyr Ser Ser Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Ser Ser Tyr Tyr Ser Ser
1               5

<210> SEQ ID NO 12
<211> LENGTH: 6
<212> TYPE: PRT
<213> ORGANISM: Artificial Sequence
```

<220> FEATURE:
<223> OTHER INFORMATION: Synthetic peptide

<400> SEQUENCE: 12

Ser Ser Ser Tyr Tyr Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Ser Ser Ser Ser Tyr Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Trp Ser Tyr Ser Ser Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Ser Trp Ser Tyr Ser Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Ser Ser Trp Ser Tyr Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Ser Ser Ser Trp Ser Tyr
1               5

<210> SEQ ID NO 18
<211> LENGTH: 6
<212> TYPE: PRT
<213> ORGANISM: Artificial Sequence
<220> FEATURE:

<223> OTHER INFORMATION: Synthetic peptide

<400> SEQUENCE: 18

Tyr Ser Ser Ser Trp Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Ser Tyr Ser Ser Ser Trp
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Trp Tyr Trp Tyr Trp Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Tyr Trp Tyr Trp Tyr Trp
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Ser Ser Ser Ser Ser Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Gln Gln Tyr Asn Asn Trp
1               5

<210> SEQ ID NO 24
<211> LENGTH: 34
<212> TYPE: DNA
<213> ORGANISM: Artificial Sequence
<220> FEATURE:
<223> OTHER INFORMATION: Synthetic primer

```
<400> SEQUENCE: 24
ggctgcgatc gccatggagt ttgggctkag ctgg                          34

<210> SEQ ID NO 25
<211> LENGTH: 34
<212> TYPE: DNA
<213> ORGANISM: Artificial Sequence
<220> FEATURE:
<223> OTHER INFORMATION: Synthetic primer

<400> SEQUENCE: 25
atgcgtttaa actttacccg gagacaggga gagg                          34

<210> SEQ ID NO 26
<211> LENGTH: 37
<212> TYPE: DNA
<213> ORGANISM: Artificial Sequence
<220> FEATURE:
<223> OTHER INFORMATION: Synthetic primer

<400> SEQUENCE: 26
ggctgcgatc gccatggaac catggaagcc ccagcac                       37

<210> SEQ ID NO 27
<211> LENGTH: 35
<212> TYPE: DNA
<213> ORGANISM: Artificial Sequence
<220> FEATURE:
<223> OTHER INFORMATION: Synthetic primer

<400> SEQUENCE: 27
gggggtttaa acacactctc ccctgttgaa gctct                         35

<210> SEQ ID NO 28
<211> LENGTH: 384
<212> TYPE: DNA
<213> ORGANISM: Artificial Sequence
<220> FEATURE:
<223> OTHER INFORMATION: C3 clone

<400> SEQUENCE: 28
atggaagccc cagctcagct tctcttcctc ctgctactct ggctcccaga ctgcaccgga    60
gaaattgtct tgacgcagtc tccaggcacc ctgtctttgt ctccagggga aagagccacc   120
ctctcctgca gggccagtca gagtgttagc agcaacttag cctggtacca gcagaaacct   180
ggccaggctc ccaggctcct catctatggt gcatccacca gggccactgg tatcccagcc   240
aggttcagtg gcagtgggtc tgggacagag ttcactctca ccatcagcag cctgcagtct   300
gaagattttg cagtttatta ctgtcagcag tataataact ggcctccgct cactttcggc   360
ggagggacca aggtggagat caaa                                         384

<210> SEQ ID NO 29
<211> LENGTH: 128
<212> TYPE: PRT
<213> ORGANISM: Artificial Sequence
<220> FEATURE:
<223> OTHER INFORMATION: Synthetic protein

<400> SEQUENCE: 29

Met Glu Ala Pro Ala Gln Leu Leu Phe Leu Leu Leu Trp Leu Pro
1               5                   10                  15

Asp Cys Thr Gly Glu Ile Val Leu Thr Gln Ser Pro Gly Thr Leu Ser
```

```
            20                  25                  30
Leu Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Leu Thr Phe Gly Gly Gly Thr Lys Val Glu Ile Lys
        115                 120                 125
```

<210> SEQ ID NO 30
<211> LENGTH: 411
<212> TYPE: DNA
<213> ORGANISM: Artificial Sequence
<220> FEATURE:
<223> OTHER INFORMATION: E6 clone

<400> SEQUENCE: 30

```
atggagtttg gcttagctg  gatcttcctt gttgctattc taaaaggtgt ccagtgtgac    60
gtgcagttgg tggagtctgg gggaggtgtg gtccggcctg ggagtccct  gagactctcc   120
tgtgcagcct ctggattcac ctttaccaat tatgacatga gttgggtccg ccaggctcca   180
ggggaggggc tggagtgggt ctcagctatt agtggtagtg gtgataccac atactacgca   240
gactccgtga agggccggtt caccatctcc agagacaatt ccaagaacac tctctatctg   300
cgcctgttca gcctgagagc cgaggacacg gccatttatt actgtgcgaa agggacctgg   360
aacactttct ttgactactg gggcctggga accctggtca ccgtctcctc a            411
```

<210> SEQ ID NO 31
<211> LENGTH: 137
<212> TYPE: PRT
<213> ORGANISM: Artificial Sequence
<220> FEATURE:
<223> OTHER INFORMATION: Synthetic protein

<400> SEQUENCE: 31

```
Met Glu Phe Gly Leu Ser Trp Ile Phe Leu Val Ala Ile Leu Lys Gly
1               5                  10                  15

Val Gln Cys Asp Val Gln Leu Val Glu Ser Gly Gly Gly Val Val Arg
            20                  25                  30

Pro Gly Glu Ser Leu Arg Leu Ser Cys Ala Ala Ser Gly Phe Thr Phe
        35                  40                  45

Thr Asn Tyr Asp Met Ser Trp Val Arg Gln Ala Pro Gly Glu Gly Leu
    50                  55                  60

Glu Trp Val Ser Ala Ile Ser Gly Ser Gly Asp Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Arg Leu Phe Ser Leu Arg Ala Glu Asp Thr Ala Ile
            100                 105                 110

Tyr Tyr Cys Ala Lys Gly Thr Trp Asn Thr Phe Phe Asp Tyr Trp Gly
        115                 120                 125

Leu Gly Thr Leu Val Thr Val Ser Ser
```

<210> SEQ ID NO 32
<211> LENGTH: 21
<212> TYPE: DNA
<213> ORGANISM: Artificial Sequence
<220> FEATURE:
<223> OTHER INFORMATION: Synthetic primer

<400> SEQUENCE: 32
actgtgctgc aggtggctat g                                           21

<210> SEQ ID NO 33
<211> LENGTH: 23
<212> TYPE: DNA
<213> ORGANISM: Artificial Sequence
<220> FEATURE:
<223> OTHER INFORMATION: Synthetic primer

<400> SEQUENCE: 33
atacgatgtt ccagattacg ctt                                         23

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
gcgctgactc agccgtcctc                                             20

<210> SEQ ID NO 35
<211> LENGTH: 21
<212> TYPE: DNA
<213> ORGANISM: Artificial Sequence
<220> FEATURE:
<223> OTHER INFORMATION: Synthetic primer

<400> SEQUENCE: 35
gagacgaggt cagcgactca c                                           21

<210> SEQ ID NO 36
<211> LENGTH: 25
<212> TYPE: DNA
<213> ORGANISM: Artificial Sequence
<220> FEATURE:
<223> OTHER INFORMATION: Synthetic primer

<400> SEQUENCE: 36
ctctgctaac catgttcatg ccttc                                       25

<210> SEQ ID NO 37
<211> LENGTH: 22
<212> TYPE: DNA
<213> ORGANISM: Artificial Sequence
<220> FEATURE:
<223> OTHER INFORMATION: Synthetic primer

<400> SEQUENCE: 37
agtgacaacg tcgagcacag ct                                          22

<210> SEQ ID NO 38
<211> LENGTH: 23
<212> TYPE: DNA
<213> ORGANISM: Artificial Sequence

```
<220> FEATURE:
<223> OTHER INFORMATION: Synthetic primer

<400> SEQUENCE: 38
cgcacacgta taacatccat gaa                                           23

<210> SEQ ID NO 39
<211> LENGTH: 22
<212> TYPE: DNA
<213> ORGANISM: Artificial Sequence
<220> FEATURE:
<223> OTHER INFORMATION: Synthetic primer

<400> SEQUENCE: 39
gtgtgagatg cagacagcac gc                                            22

<210> SEQ ID NO 40
<211> LENGTH: 22
<212> TYPE: DNA
<213> ORGANISM: Artificial Sequence
<220> FEATURE:
<223> OTHER INFORMATION: Synthetic primer

<400> SEQUENCE: 40
atggaagccc cagctcagct tc                                            22

<210> SEQ ID NO 41
<211> LENGTH: 22
<212> TYPE: DNA
<213> ORGANISM: Artificial Sequence
<220> FEATURE:
<223> OTHER INFORMATION: Synthetic primer

<400> SEQUENCE: 41
caggtagctg ctggccatat ac                                            22

<210> SEQ ID NO 42
<211> LENGTH: 21
<212> TYPE: DNA
<213> ORGANISM: Artificial Sequence
<220> FEATURE:
<223> OTHER INFORMATION: Synthetic primer

<400> SEQUENCE: 42
aacaccccag ccatgtatgt a                                             21

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
tttcattgtg ctaggtgcca                                               20
```

TRANSGENIC ANIMAL FOR PRODUCTION OF ANTIBODIES HAVING MINIMAL CDRS

CROSS-REFERENCING

This application is a continuation of U.S. patent application Ser. No. 16/209,807, filed on Dec. 4, 2018, which is a continuation of U.S. patent application Ser. No. 15/996,373, filed on Jun. 1, 2018, now issued as U.S. Pat. No. 10,172,334, which is a continuation of U.S. patent application Ser. No. 15/377,940, filed on Dec. 13, 2016, now issued as U.S. Pat. No. 10,010,058, which is a continuation of U.S. patent application Ser. No. 15/188,724, filed on Jun. 21, 2016, now issued as U.S. Pat. No. 9,549,538, which is a divisional of U.S. patent application Ser. No. 14/057,820, filed on Oct. 18, 2013, now issued as U.S. Pat. No. 9,404,125, which is a divisional of U.S. patent application Ser. No. 12/854,722, filed on Aug. 11, 2010, now issued as U.S. Pat. No. 8,592,644, which claims the priority benefit of U.S. provisional application Ser. No. 61/274,319, filed Aug. 13, 2009, all of which are incorporated by reference herein in their entirety.

BACKGROUND

Antibodies are proteins that bind a specific antigen. Generally, antibodies are specific for their targets, have the ability to mediate immune effector mechanisms, and have a long half-life in serum. Such properties make antibodies powerful therapeutics. Monoclonal antibodies are used therapeutically for the treatment of a variety of conditions including cancer, inflammation, and cardiovascular disease. There are currently over twenty therapeutic antibody products on the market and hundreds in development.

There is a constant need for new antibodies and methods for making the same.

SUMMARY

A transgenic non-human animal is provided. In certain embodiments, the transgenic animal comprises a genome comprising: an immunoglobulin light chain locus comprising: a) a functional immunoglobulin light chain gene comprising a transcribed variable region encoding: i. light chain CDR1, CDR2 and CDR3 regions that are composed of 2 to 5 different amino acids; and ii. a light chain framework; and, operably linked to the functional immunoglobulin light chain gene: b) a plurality of pseudogene light chain variable regions each encoding: i. light chain CDR1, CDR2 and CDR3 regions that are composed of the same 2 to 5 different amino acids as the CDRs of the functional gene; and ii. a light chain framework that is identical in amino acid sequence to the light chain framework of the transcribed variable region, where the plurality of pseudogene light chain variable regions donate nucleotide sequence to the transcribed variable region of the functional immunoglobulin light chain gene by gene conversion in the transgenic animal.

In addition or as an alternative to the above, the transgenic animal may comprise an immunoglobulin heavy chain locus comprising: a) a functional immunoglobulin heavy chain gene comprising a transcribed variable region encoding: i. heavy chain CDR1, CDR2 and CDR3 regions that are composed of 2 to 5 different amino acids (e.g., the same 2 to 5 amino acids as the light chain); and ii. a heavy chain framework; and, operably linked to the functional immunoglobulin heavy chain gene: b) a plurality of pseudogene heavy chain variable regions each encoding: i. heavy chain CDR1, CDR2 and CDR3 regions that are composed of the same 2 to 5 different amino acids as the functional gene; and ii. a heavy chain framework that is identical in amino acid sequence to the heavy chain framework of the transcribed variable region, where the plurality of pseudogene heavy chain variable regions donate nucleotide sequence to the transcribed variable region of the functional immunoglobulin heavy chain gene by gene conversion in the transgenic animal.

Also provided are methods of producing and method of using the transgenic animal, as well as antibody compositions produced by the same.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 is a table showing the expression levels of various heavy and light chain sequences.

DEFINITIONS

Figure 1:
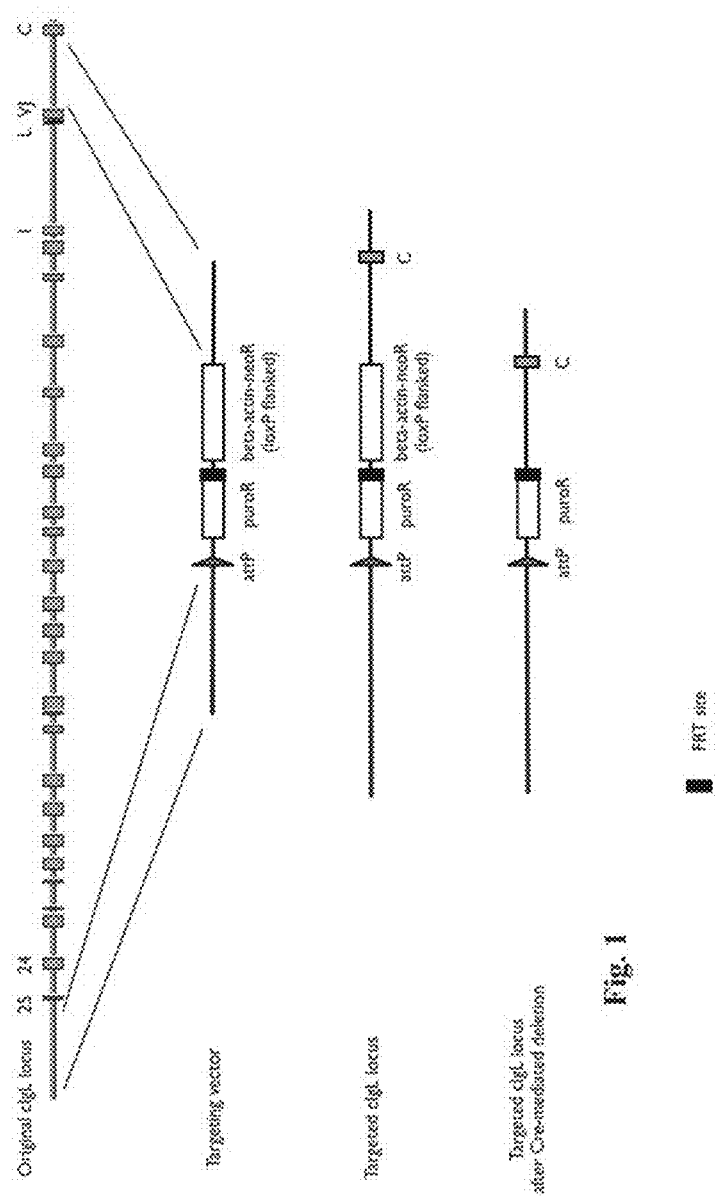
FIG. 1 schematically illustrates a strategy for deleting a chicken immunoglobulin light chain locus.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

A "leader sequence" is a sequence of amino acids present at the N-terminal portion of a protein which facilitates the secretion of the mature form of the protein from the cell. The definition of a signal sequence is a functional one. The mature form of the extracellular protein lacks the signal sequence, which is cleaved off during the secretion process.

The term "nucleic acid" encompasses DNA, RNA, single stranded or double stranded and chemical modifications thereof. The terms "nucleic acid" and "polynucleotide" are used interchangeably herein.

A "non-human" animal refers to any animal of a species that is not human.

The term "progeny" or "off-spring" refers to any and all future generations derived and descending from a particular animal. Thus, progeny of any successive generation are included herein such that the progeny, the F1, F2, F3, generations and so on are included in this definition.

The phrase "transgenic animal" refers to an animal comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell.

The term "intron" refers to a sequence of DNA found in the middle of many gene sequences in most eukaryotes. These intron sequences are transcribed, but removed from within the pre-mRNA transcript before the mRNA is translated into a protein. This process of intron removal occurs by splicing together of the sequences (exons) on either side of the intron.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. In the context of gene conversion, two nucleic acids sequences are operably linked if one sequence can "donate" sequence to the other by gene conversion. If two sequences are unlinked in that one can donate sequence to the other via gene conversion, the donating sequences may be upstream or downstream of the other, and the two sequences may be proximal to each other, i.e., in that there are no other intervening genes. "Unlinked" means that the associated genetic elements are not closely associated with one another and the function of one does not affect the other.

The terms "upstream" and "downstream" are used with reference to the direction of transcription.

The term "pseudogene" is used to describe an untranscribed nucleic acid region that contains an open reading frame that may or may not contain a start and/or a stop codon. An amino acid sequence may be "encoded" by a pseudogene in the sense that the nucleotide sequence of the open reading frame can be translated in silico to produce an amino acid sequence. In the context of the heavy and light chain immunoglobulin loci, pseudogenes do not contain promoter regions, recombination signal sequences or leader sequences.

The term "homozygous" indicates that identical alleles reside at the same loci on homologous chromosomes. In contrast, "heterozygous" indicates that different alleles reside at the same loci on homologous chromosomes. A transgenic animal may be homozygous or heterozygous for a transgene.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence (s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or 'transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "replacing", in the context of replacing one genetic locus with another, refers to a single step protocol or multiple step protocol.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA. Pseudogenes may contain an untranscribed coding sequence.

The term "in reverse orientation to" refers to coding sequences that are on different strands. For example, if a transcribed region is described as being in reverse orientation to a pseudogene, then the amino acid sequence encoded by the transcribed region is encoded by the top or bottom strand and the amino acid sequence encoded by the pseudogene is encoded by the other strand relative to the transcribed region. As illustrated in FIG. 8, the orientation of a coding sequence may be indicated by an arrow.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, $F(ab')_2$, and or other antibody fragments that retain specific binding to antigen, and monoclonal antibodies.

Antibodies may exist in a variety of other forms including, for example, Fv, Fab, and $(Fab')_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),).

An immunoglobulin light or heavy chain variable region consists of a "framework" region (FR) interrupted by three hypervariable regions, also called "complementarity determining regions" or "CDRs". The extent of the framework region and CDRs have been precisely defined (see, Lefranc et al, IMGT, the international ImMunoGeneTics information system. Nucleic Acids Res. 2009 vol. 37 (Database issue): D1006-12. Epub 2008 Oct. 31; see worldwide website of imgt.org and referred to hereinafter as the "IMGT sytem")). The numbering of all antibody amino acid sequences discussed herein conforms to the IMGT system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a chicken or rabbit monoclonal antibody may be joined to human constant segments, such as gamma 1 and gamma 3. An example of a therapeutic chimeric antibody is a hybrid protein composed of the variable or antigen-binding domain from a chicken or rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "human framework" refers to a framework that has an amino acid sequence that is at least 90% identical, e.g., at least 95%, at least 98% or at least 99% identical to the amino acid sequence of a human antibody, e.g., the amino acid sequence of a human germ-line sequence of an antibody. In certain cases, a human framework may be a fully human framework, in which case the framework has an amino acid sequence that is identical to that of a human antibody, e.g., a germ-line antibody.

As used herein, the term "humanized antibody" or "humanized immunoglobulin" refers to a non-human antibody containing one or more amino acids (in a framework region, a constant region or a CDR, for example) that have been substituted with a correspondingly positioned amino acid from a human antibody. In general, humanized antibodies are expected to produce a reduced immune response in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between an antibody and analyte when they are specifically bound in an antibody/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

A "variable region" of a heavy or light antibody chain is an N-terminal mature domain of the chain that contains CDR1, CDR2 and CD3, and framework regions. The heavy and light chain of an antibody both contain a variable domain. All domains, CDRs and residue numbers are assigned on the basis of sequence alignments and structural knowledge. Identification and numbering of framework and CDR residues is as defined by the IMGT system.

VH is the variable domain of an antibody heavy chain. VL is the variable domain of an antibody light chain.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

The terms "treatment" "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

A "natural" antibody is an antibody in which the heavy and light immunoglobulins of the antibody have been naturally selected by the immune system of a multi-cellular organism, as opposed to unnaturally paired antibodies made by e.g. phage display. As such, the certain antibodies do not contain any viral (e.g., bacteriophage M13)-derived sequences. Spleen, lymph nodes and bone marrow are examples of tissues that produce natural antibodies in an animal.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

Further definitions may be elsewhere in this disclosure.

DESCRIPTION OF EXEMPLARY EMBODIMENTS

A transgenic animal is provided. In certain embodiments, the transgenic animal comprises a genome comprising: an immunoglobulin locus comprising: a) a functional immunoglobulin gene comprising a transcribed variable region encoding: i. CDR1, CDR2 and CDR3 regions that are composed of 2 to 5 different amino acids; and ii. a framework region; and, operably linked to the functional immunoglobulin gene: b) a plurality of pseudogene light chain variable regions each encoding: i. CDR1, CDR2 and CDR3 regions that are composed of the same 2 to 5 different amino acids as the functional gene; and ii. a framework region that is identical in amino acid sequence to the framework region of the transcribed variable region, where the plurality of pseudogene variable regions donate nucleotide sequence to the transcribed variable region of the functional immunoglobulin gene by gene conversion in the transgenic animal. The immunoglobulin locus may be an immunoglobulin light chain locus or an immunoglobulin heavy chain locus. In certain cases, the animal may contain both heavy and light chain loci as described herein.

Before the present subject invention is described further, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Transgenic Animals

As noted above, a transgenic animal is provided. In certain embodiments, the animal may be any non-human animal that employs gene conversion for developing their primary antigen repertoire and, as such, the animal may be any of a variety of different animals. In one embodiment, the animal may be a bird, e.g., a member of the order Galliformes such as a chicken or turkey, or a member of the order Anseriformes such as a duck or goose, or a mammal, e.g., a lagamorph such as rabbit, or a farm animal such as a cow, sheep, pig or goat. In particular embodiments, the transgenic animal may be a non-rodent (e.g., non-mouse or non-rat), non-primate transgenic animal.

Some of this disclosure relates to a transgenic chicken containing one or more transgenes that encode an array of synthetic variable regions. Since the nucleotide sequences of the immunoglobulin loci of many animals are known, as are methods for modifying the genome of such animals, the general concepts described below may be readily adapted to any suitable animal, i.e., any animal that employs gene conversion for developing their primary antigen repertoire. The generation of antibody diversity by gene conversion between the variable region of a transcribed immunoglobulin heavy or light chain gene and operably linked (upstream) pseudo-genes that contain different variable regions is described in a variety of publications such as, for example, Butler (Rev. Sci. Tech. 1998 17: 43-70), Bucchini (Nature 1987 326: 409-11), Knight (Adv. Immunol. 1994 56: 179-218), Langman (Res. Immunol. 1993 144: 422-46), Masteller (Int. Rev. Immunol. 1997 15: 185-206), Reynaud (Cell 1989 59: 171-83) and Ratcliffe (Dev. Comp. Immunol. 2006 30: 101-118).

In certain embodiments, the transgenic animal contains a functional immunoglobulin light chain gene that is expressed (i.e., transcribed to produce an mRNA that is subsequently translated) to produce a light chain of an antibody, and, operably linked to (which, in the case is chicken and many other species is immediately upstream of) the functional light chain gene, a plurality of different pseudogene light chain variable regions, where the variable regions of the pseudogenes are operably linked to the functional immunoglobulin light chain in that they the alter the sequence of the functional immunoglobulin light chain gene by gene conversion (i.e., by substituting a sequence of the functional immunoglobulin light chain gene variable region with a sequence of a pseudogene variable region). In the transgenic animal, gene conversion between the functional immunoglobulin light chain gene variable region and a pseudogene variable region alters the sequence of the functional immunoglobulin light chain gene variable region by as little as a single codon up to the entire length of the variable region. In certain cases a pseudogene variable region may donate the sequence of at least one CDR (e.g., CDR1, CDR2 or CDR3) from a pseudogene variable region in to the variable region of the functional gene. The light chains of the antibodies produced by the transgenic animal are therefore encoded by whatever sequence is donated from the pseudogene variable regions into the variable region of the functional light chain gene.

Likewise, the transgenic animal may also contain an a functional immunoglobulin heavy chain gene that is transcribed and translated to produce a heavy chain of an antibody, and, operably linked to (e.g., immediately upstream of) the functional heavy chain gene, a plurality of different pseudogene heavy chain variable regions, where the variable regions of the pseudogenes are operably linked to the functional immunoglobulin light chain in that they alter the sequence of the functional immunoglobulin heavy chain gene by gene conversion. In the transgenic animal, gene conversion between the functional immunoglobulin heavy chain gene variable region and a pseudogene variable region alters the sequence of the functional immunoglobulin heavy chain gene variable region by as little as a single codon up to the entire length of the variable region. In certain cases may a pseudogene variable region may donate the sequence of at least one CDR (e.g., CDR1, CDR2 or CDR3) from a pseudogene variable region to the variable region of the functional gene. The heavy chains of the antibodies produced by the transgenic animal are therefore encoded by whatever sequence is donated from the pseudogene variable regions into the variable region of the functional heavy chain gene.

The antibodies produced by the transgenic animal are therefore encoded by whatever sequences are donated from the pseudogene variable regions to the variable region of the functional gene. Since different sequences are donated in different cells of the animal, the antibody repertoire of the animal is determined by which sequences are donated from the pseudogene variable regions to the variable region of the functional gene.

In particular embodiments, the framework encoded by the variable region pseudogenes is identical in amino acid sequence to the framework region of the functional gene to which the pseudogenes are operably linked. In other words, the amino acid sequence of all of the FR1 regions encoded by the pseudogenes may be identical to the FR1 region encoded by the transcribed variable domain, the amino acid sequence of all of the FR2 regions encoded by the pseudogenes may be identical to the FR2 region encoded by the transcribed variable domain, the amino acid sequence of all of the FR3 regions encoded by the pseudogenes may be identical to the FR3 region encoded by the transcribed variable domain and the amino acid sequence of all of the FR4 regions encoded by the pseudogenes may be identical to the FR4 region encoded by the transcribed variable domain, thereby allowing the production of an antibody with a defined heavy and/or light chain framework.

In particular embodiments, the nucleotide sequences encoding the framework of the variable region pseudogenes may be identical to the nucleotide sequences encoding the framework of the functional gene to which the pseudogenes are operably linked. In other words, the nucleotide sequence encoding all of the FR1 regions in the pseudogenes may be identical to the nucleotide sequence encoding the FR1 region of the transcribed variable domain, the nucleotide sequence encoding all of the FR2 regions in the pseudogenes may be identical to the nucleotide sequence encoding the FR2 region of the transcribed variable domain, the nucleotide sequence encoding all of the FR3 regions in the pseudogenes may be identical to the nucleotide sequence encoding the FR3 region of the transcribed variable domain and the nucleotide sequence encoding all of the FR4 regions in the pseudogenes may be identical to the nucleotide sequence encoding the FR4 region of the transcribed variable domain, thereby resulting in an functional gene with a defined nucleotide sequence.

The chosen framework sequence may be human, e.g., have a sequence that is at least 90%, at least 95%, at least 98%, at least 99% or 100% identical to the germ-line sequence of a human antibody, thereby allowing production of an antibody containing a human framework.

In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, the light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. See PCT WO 2005/005604 for a description of the different germline sequences.

In other embodiments, the heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. See PCT WO 2005/005604 for a description of the different germline sequences.

In some embodiments, the nucleotide sequence and/or amino acid sequence of the introduced transcribed variable region may be human, i.e., may contain the nucleotide and/or amino acid sequence of a human antibody or germline sequence. In these embodiments, both the CDRs and the framework may be human. In other embodiments, the the nucleotide sequence and/or amino acid sequence of the introduced transcribed variable region is not human and may instead be at least 80% identical, at least 90% identical, at least 95% or more identical to a human sequence. For example, relative to a human sequence, the introduced transcribed variable region may contain one or more nucleotide or amino acid substitution. In particular embodiments, the nucleotide sequence of the introduced transcribed variable region may be at least 80% identical, at least 90% identical, at least 95% or more identical to the variable regions shown in FIGS. 11 and 12. In one embodiment, the framework sequence used contains one, two, three, four or five or more substitutions relative the the framework sequence shown in FIGS. 11 and 12.

In particular embodiments, part of the light chain locus that includes the constant domain-encoding region, part of an intron, and the 3'UTR of the functional gene may be endogenous to the animal and the remainder of the light chain locus, including the variable regions of the functional gene, the remainder of the intron and the pseudogenes may be exogenous to the animal, i.e., made recombinantly and introduced into the animal proximal to the constant domain, part intron and 3' UTR in such a way that a functional light chain gene is produced and the pseudogenes are capable of donating sequence to the functional light chain gene by gene conversion. In certain cases the light chain locus of the animal may contain, in operable linkage: an intron region, a constant domain-encoding region and a 3' untranslated region; where the intron region, the constant domain-encoding region and the 3' untranslated region are endogenous to the genome of the transgenic animal and a plurality of pseudogene light chain variable regions, where the plurality of pseudogene light chain variable regions are exogenous to the genome of the transgenic animal. Alternatively, the constant domain encoding region could also be exogenous to the genome of the transgenic animal.

Likewise, part of the heavy chain locus, including the constant region, part of an intron region and the 3'UTR of the functional gene, may be endogenous to the animal and the remainder of the heavy chain locus, including the variable domains of the functional gene, the remainder of the intron and the pseudogenes may be exogenous to the animal, i.e., made recombinantly and introduced into the animal proximal to the constant domain, part intron and 3' UTR in such a way that a functional gene is produced and the pseudogenes are capable of donating sequence to the functional gene by gene conversion. In certain cases the heavy chain locus of the animal may contain, in operable linkage: an intron region, a constant domain-encoding region and a 3' untranslated region, where the intron region, the constant domain-encoding region and the 3' untranslated region are endogenous to the genome of the transgenic animal, and a plurality of pseudogene heavy chain variable regions, where the plurality of pseudogene heavy chain variable regions are exogenous to the genome of the transgenic animal.

In certain embodiments, an antibody produced by a subject transgenic animal may contain an endogenous constant domain and variable domains that are exogenous to the animal. Since an endogenous constant region may be employed in these embodiments, the antibody may still undergo class switching and affinity maturation, which allows the animal to undergo normal immune system development, and mount normal immune responses. In specific embodiments transgenic chickens have three endogenous constant regions in the heavy chain locus encoding IgM, IgY and IgA. During the early stages of B cell development, B cells express IgM. As affinity maturation proceeds, class switching converts the constant region into IgY or IgA. IgY provides humoral immunity to both adults and neonatal chicks which receive about 200 mg of IgY via a reserve deposited into egg yolk. IgA is found primarily in lymphoid tissues (eg. the spleen, Peyer's patches and Harderian glands) and in the oviduct.

While, as noted above, the encoded framework regions of the variable regions of both the pseudogenes and the functional gene of the light chain locus may be identical to one another, the CDR regions encoded by the variable regions in each of the pseudogenes are different to one another (i.e., each of the plurality of pseudogenes encodes a CDR1 region that is different to the amino acid sequences of all the other CDR1 regions, each of the plurality of pseudogenes encodes a CDR2 region that is different to the amino acid sequences of all the other CDR2 regions, and each of the plurality of pseudogenes encodes a CDR3 region that is different to the amino acid sequences of all the other CDR3 regions). Likewise for the heavy chain locus, the CDR regions encoded by the variable regions in each of the pseudogenes are different to one another.

In certain cases, the CDR regions encoded by the light chain variable domain, and/or the heavy chain variable domain may be composed of only 2 to 5 (i.e., 2, 3, 4, or 5) different amino acid residues, where, in this context, the term "composed of" is intended to mean that each individual amino acid position within a CDR is occupied by a single amino acid residue independently chosen from a group of 2 to 5 amino acid residues. Examples of CDRs that are composed of 2-5 amino acids are described in the Examples section of this disclosure. In certain embodiments, at least one of the 2 to 5 amino acids is a bulky amino acid such as a tyrosine or tryptophan residue, and at least one of said 2 to 5 amino acids is a small amino acid residue such as an alanine, glycine or serine residue.

CDRs may vary in length. In certain embodiments, the heavy chain CDR1 may be in the range of 6 to 12 amino acid residues in length, the heavy chain CDR2 may be in the range of 4 to 12 amino acid residues in length, the heavy chain CDR3 may be in the range of 3 to 25 amino acid residues in length, the light chain CDR1 may be in the range of 4 to 14 amino acid residues in length, the light chain CDR2 may be in the range of 2 to 10 amino acid residues in length, the light chain CDR3 may be in the range of 5 to 11 amino acid residues in length, although antibodies having CDRs of lengths outside of these ranges are envisioned.

With the exception of a relatively small number of amino acids arising as a result of mutations that occur independently of gene conversion during affinity maturation (which occur in, e.g., less than 10%, less than 5%, less then 3%, or less than 1% of the amino acids), the resultant antibodies produced by the transgenic animal may have light and/or heavy chain CDRs that are solely composed of the 2 to 5 different amino acids. In exemplary embodiments, the CDRs are composed of 25% to 75% (e.g., 40% to 60%) bulky amino acids selected from tyrosine and tryptophan, and 25% to 75% (e.g., 40% to 60%) small amino acids selected from alanine, glycine and serine, with the remainder (i.e., less than 10%, less than 5%, less then 3%, or less than 1% of the amino acids), being any of the other naturally occurring amino acids. The particular order of the amino acids in each CDRs of the pseudogenes may be randomly generated.

The number of introduced pseudogene variable regions present at the light and/or heavy chain locus may vary and, in particular embodiments, may be in the range of 5-30, e.g., 10 to 25. In particular embodiments, at least one (e.g., at least 2, at least 3, at least 5, at least 10 or more) of the plurality of pseudogene light chain variable regions may be in reverse orientation relative to the transcribed light chain variable region. Likewise, in particular embodiments, at least one (e.g., at least 2, at least 3, at least 5, at least 10 or more) of the plurality of pseudogene heavy chain variable regions may be in reverse orientation relative to the heavy chain transcribed variable region. In particular embodiments, the plurality of pseudogene variable regions are not in alternating orientations, and in certain cases may (as illustrated in FIG. 8) rather contain a series of at least 5 or at least 10 adjacent pseudogene regions that are in opposite orientation relative to the transcribed variable region. In one embodiment, the pseudogene region that is most distal from the transcribed variable region is in the same orientation as the transcribed variable region, and the pseudogene regions between the most distal region and the transcribed variable region are in the reverse orientation relative to the transcribed variable region.

The above-described transgenic animal may be made by replacing the endogenous variable regions in an endogenous immunoglobulin light chain locus and/or heavy chain locus of animal with a plurality of pseudogene light chain variable regions constructed recombinantly. Methods for producing transgenic animals that use gene conversion to generate an antibody repertoire are known (see, e.g., Sayegh, Vet. Immunol. Immunopathol. 1999 72:31-7 and Kamihira, Adv. Biochem. Eng. Biotechnol. 2004 91: 171-89 for birds, and Bosze, Transgenic Res. 2003 12:541-53 and Fan, Pathol. Int. 1999 49: 583-94 for rabbits and Salamone J. Biotechnol. 2006 124: 469-72 for cow), as is the structure and/or sequence of the germline immunoglobulin heavy and light chain loci of many of those species (e.g., Butler Rev Sci Tech 1998 17:43-70 and Ratcliffe Dev Comp Immunol 2006 30: 101-118), the above-described animal may be made by routine methods given this disclosure.

A method of making a transgenic animal is provided. In certain embodiments, the method comprises: replacing the variable regions in the endogenous immunoglobulin light chain locus of a suitable animal with a nucleic acid construct comprising: a) a light chain variable region encoding: i. light chain CDR1, CDR2 and CDR3 regions that are composed of 2 to 5 different amino acids; and ii. light chain framework regions; and b) a plurality of pseudogene light chain variable regions each encoding: i. light chain CDR1, CDR2 and CDR3 regions that are composed of the 2 to 5 different amino acids; and ii. light chain framework regions that are identical to the corresponding framework regions encoded by the light chain variable region. Upon integration of the construct, the light chain variable region becomes the transcribed variable region of the functional immunoglobulin locus of the transgenic animal, and the pseudogene variable regions alter the sequence of the transcribed V region by gene conversion. In particular embodiments, the engineered locus is designed to fully replace the endogenous V region, including pseudo-V's, the transcribed V, as well as the D and J gene segments. However, non-coding sequences (introns) may be retained in endogenous configuration in order to preserve endogenous regulatory elements that may be contained within.

Likewise, the method may comprise: replacing the variable regions in the endogenous immunoglobulin heavy chain locus of the animal with a) a heavy chain variable region encoding: i. light chain CDR1, CDR2 and CDR3 regions that are composed of the 2 to 5 different amino acids; and ii. heavy chain framework regions; and b) a plurality of pseudogene heavy chain variable regions each encoding: i. heavy chain CDR1, CDR2 and CDR3 regions that are composed of the 2 to 5 different amino acids; and ii. heavy chain framework regions that are identical to the corresponding framework regions encoded by the heavy chain variable region. Upon integration of the construct, the variable region becomes the transcribed variable region of the functional immunoglobulin locus of the transgenic animal, and the pseudogene V regions alter the sequence of the transcribed variable region by gene conversion. Gene conversion may result in the contribution of small (eg 1-10 nucleotides), moderate (10-30 nucleotides), or large (>30 nucleotides) segments of DNA from one or more of the donor pseudogenes to the transcribed V region. Gene conversion can transpire over many iterations, so multiple pseudo-V's may contribute sequence to the actively expressed V gene. Since the process of gene conversion is highly variable in terms of which pseudogenes are selected, and the extent to which each is utilized in a given lymphocyte, a large and diverse antibody repertoire will result in the transgenic animal.

As would be readily apparent, the method may include first deleting a region containing the variable regions in the endogenous immunoglobulin light chain locus of the animal (including the transcribed variable region and the pseudogene variable regions, and all sequences in between) to leave, e.g., a constant region sequence and part of the intron between the constant region sequence and the transcribed variable region; and then adding the transcribed light chain variable region, the remainder of the intron, and the plurality of pseudogene light chain variable regions to the locus of the mammal.

Figure 5:
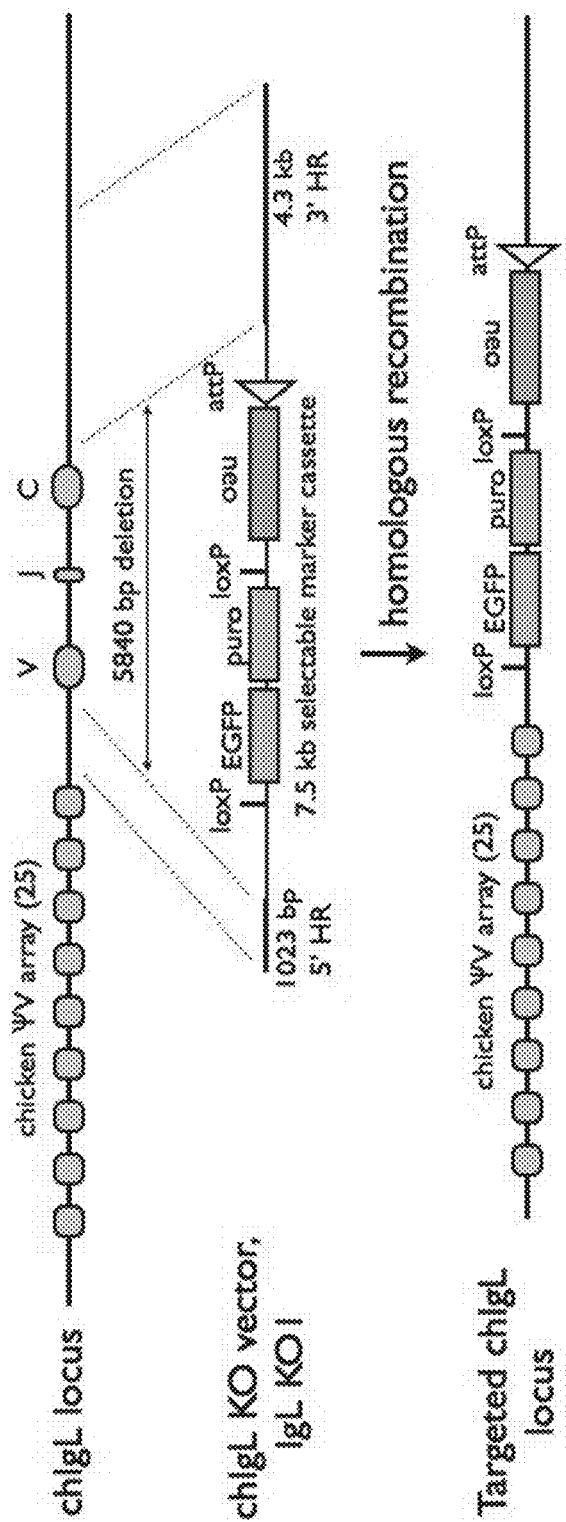
FIG. 5 schematically illustrates a strategy to place an attP site in the chicken IgL locus.
Figure 7:
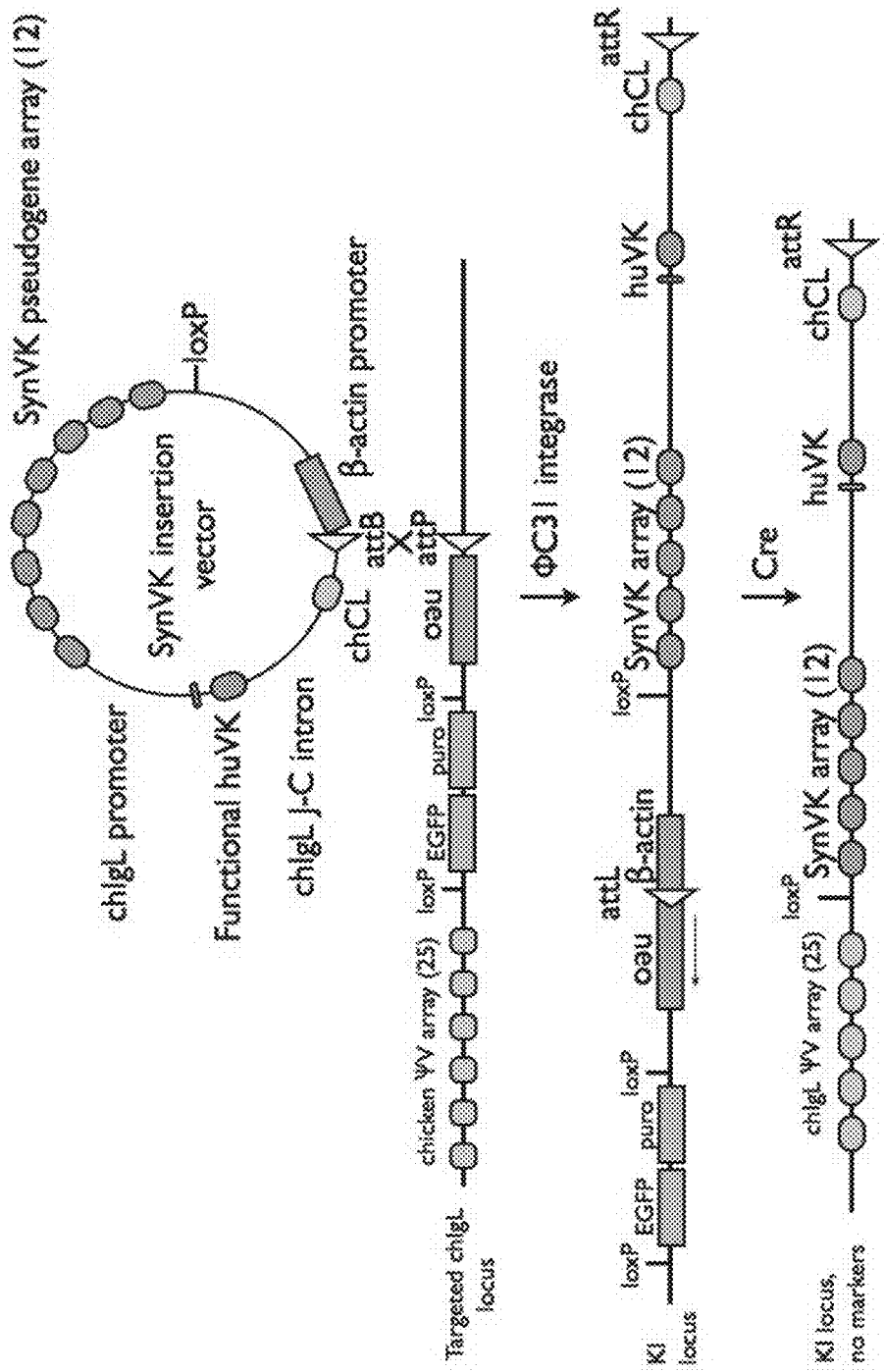
FIG. 7 schematically illustrates a strategy for making knock-ins.

In particular embodiments and as schematically illustrated in FIGS. 5 and 7, at least the variable region of the endogenous functional immunoglobulin gene of the transgenic animal may be replaced by a nucleic acid construct containing a plurality of pseudogene variable regions and a transcribed variable region, without replacing the endogenous pseudogene variable regions of said transgenic animal. As such, the resultant immunoglobulin locus (which may be the heavy or light chain locus) may contain an array of endogenous pseudogenes in addition to an array of introduced pseudogenes upstream of a transcribed variable region.

Once a subject transgenic animal is made, antibodies against an antigen can be readily obtained by immunizing the animal with the antigen. A variety of antigens can be used to immunize a transgenic host animal. Such antigens include, microorganism, e.g. viruses and unicellular organisms (such as bacteria and fungi), alive, attenuated or dead, fragments of the microorganisms, or antigenic molecules isolated from the microorganisms.

In certain embodiments, the animal may be immunized with: GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL related ligand), CA125 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HER3, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFβR (Beta platelet-derived growth factor receptor), PMSA, renal carcinoma antigen G250, RSV, E-Selectin, TGFbeta1, TGFbeta2, TNFα, DR4, DR5, DR6, VAP-1 (vascular adhesion protein 1) or VEGF, or the like in order to produce a therapeutic antibody.

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal antibody, antibody-producing cells, e.g., spleen cells, may isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1, U.S. Pat. No. 4,977,081, WO 97/16537, and EP 0 491 057 B1, the disclosures of which are incorporated herein by reference. In vitro production of monoclonal antibodies from cloned cDNA molecules has been described by Andris-Widhopf et al., J Immunol Methods 242:159 (2000), and by Burton, Immunotechnology 1:87 (1995), the disclosures of which are incorporated herein by reference.

As such, in addition to the transgenic animal, a method comprising immunizing the transgenic animal with an antigen and obtaining from the transgenic animal an antibody that specifically binds to the antigen is also provided. The method may include making hybridomas using cells of the transgenic animal; and screening the hybridomas to identify a hybridoma that produces an antibody that specifically binds to the antigen.

If the antibody does not already contain human framework regions, the method may further include humanizing the antibody, which method may include swapping the constant domain of the antibody with a human constant domain to make a chimeric antibody, as well as in certain cases humanizing the variable domains of the antibody by e.g., CDR grafting or resurfacing etc. Humanization can be done following the method of Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/:US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, including references cited therein.

Antibody Compositions

Antibody compositions are provided. An antibody may minimally have the CDRs of an antibody produced b (i.e., light chain CDR1, CDR2 and CDR3 and/or heavy chain CDR1, CDR2 and CDR3 regions of an antibody produced by a subject animal) and in the one embodiment will contain the entire variable domains (i.e., CDR plus framework) of an antibody produced by the subject animal. Such an antibody composition may contain polyclonal antisera or a monoclonal antibody that specifically binds to an antigen, methods for the production of which are known and described above.

Except for a relatively small number of amino acids that have resulted from non-gene conversion based amino acid changes to the variable domain in the functional gene during affinity maturation (i.e., which occur in less than 10%, less than 5, less than 3%, or less then 1% of the amino acids), the CDRs of the light and/or heavy chain of a subject antibody are composed the 2-5 amino acids encoded by locus described above. Likewise, the framework region is comprised of the predetermined sequence known to have desirable attributes such as monomeric form, ease of manufacturing, high solubility, and thermodynamic stability.

As noted above, the heavy and light chains variable domains of the antibody are naturally paired by the immune system of the animal. Such antibodies may, in certain case, be post-translationally modified (e.g., glycosylated) by the host cell and may have a glycosylation pattern and composition characteristic of the species of transgenic animal.

In certain embodiments, an antibody produced by the transgenic animal is provided, where the antibody comprises: a constant domain linked to a a variable domain, wherein the variable domain comprises: a) a light chain variable domain comprising: i. light chain CDR1, CDR2 and CDR3 regions that are composed of 2 to 5 different amino acids; and ii. light chain framework regions; and a) a heavy chain variable domain comprising: i. heavy chain CDR1, CDR2 and CDR3 regions that are composed of the 2 to 5 different amino acids; and ii. heavy chain framework regions.

Figure 11:
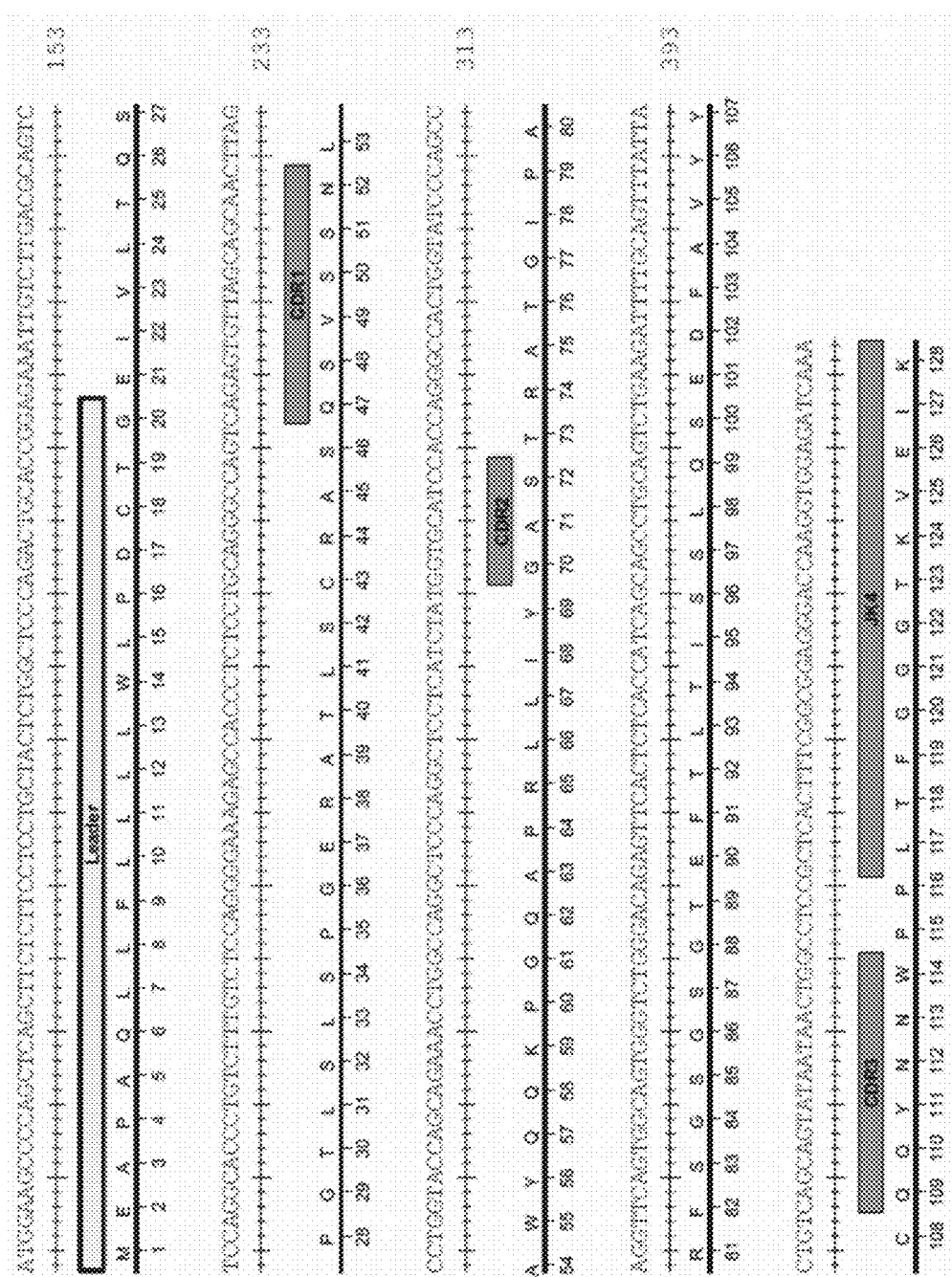
FIG. 11 shows the nucleotide sequence and encoded amino acid sequence of the E6 (light chain). SEQ ID NOS: 53 and 54.
Figure 12:
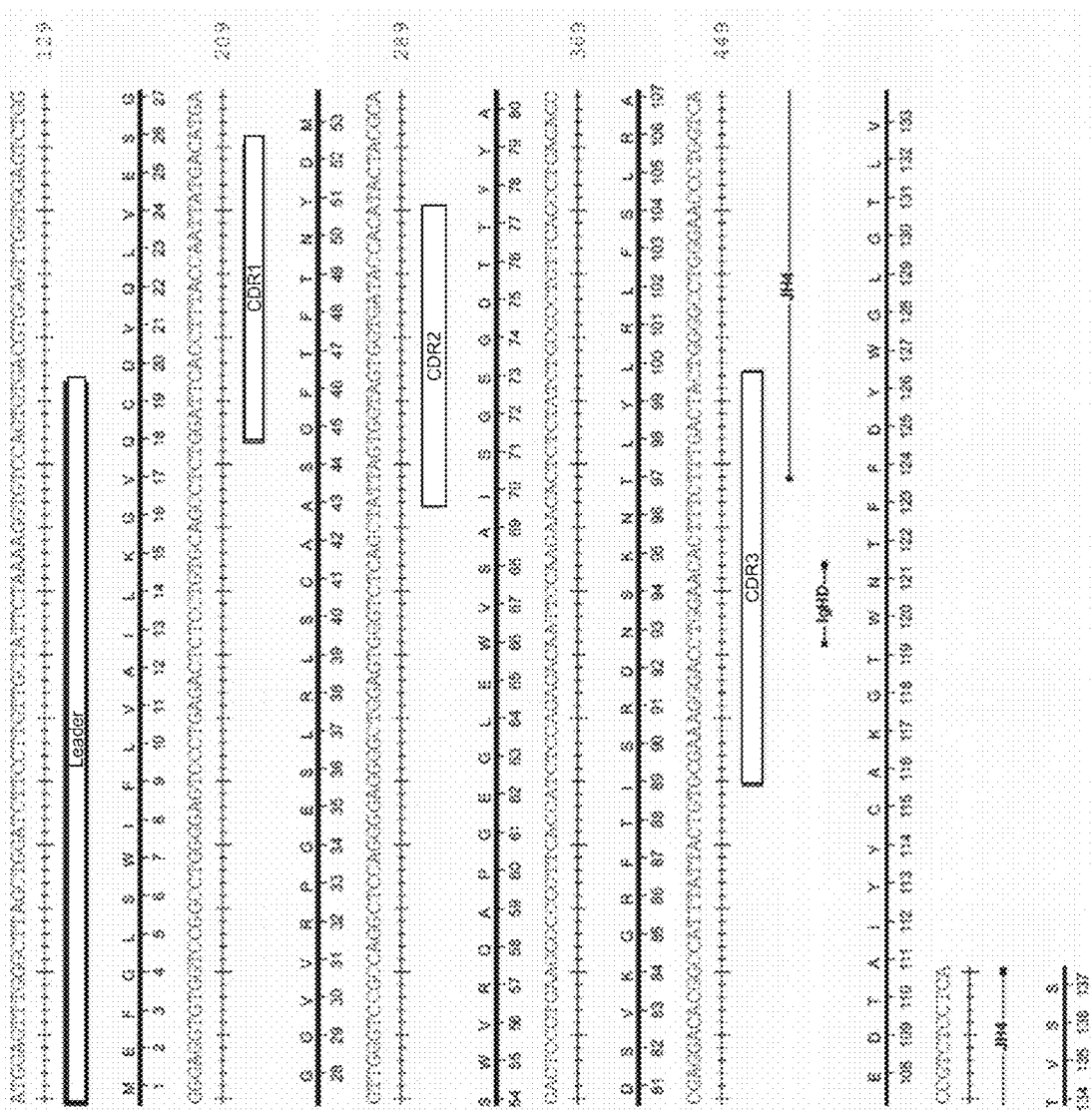
FIG. 12 shows the nucleotide sequence and encoded amino acid sequence of the C3 (heavy chain). SEQ ID NOS: 55 and 56.

In particular embodiments, the resultant antibody may have a framework that is at least 80% (e.g., at least 90%, at least 95% or more) identical to the framework of the antibody shown in FIGS. 11 and 12.

Methods of Screening

The antibodies produced by the subject transgenic animal may be screened to identify an antibody of interest. In general, this method involves producing a plurality of hybrid cells producing monoclonal antibodies using the method described above, and screening the plurality of monoclonal antibodies using one or a combination of a variety of assays. In general, these assays are functional assays, and may be grouped as follows: assays that detect an antibody's binding affinity or specificity, and assays that detect the ability of an antibody to inhibit a process.

A monoclonal antibody identified as having a specific binding activity with an antigen, or an inhibitory activity is termed a monoclonal antibody of interest.

Binding Assays

In these assays, antibodies are tested for their ability to bind specifically to a substrate. The term "specifically" in the context of antibody binding, refers to high avidity and/or high affinity binding of an antibody to a specific antigen i.e., a polypeptide, or epitope. In many embodiments, the specific antigen is an antigen (or a fragment or subfraction of an antigen) used to immunize the animal host from which the antibody-producing cells were isolated. Antibody specifically binding an antigen or fragment thereof is stronger than binding of the same antibody to other antigens. Antibodies which bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity of $10^{-7}$ M or more, e.g., $10^{-8}$ M or more (e.g., $10^{-9}$ M, $10^{-10}$, $10^{-11}$, etc.). In general, an antibody with a binding affinity of $10^{-6}$ M or less is not useful in that it will not bind an antigen at a detectable level using conventional methodology currently used.

Typically, in performing a screening assay, antibody samples produced by a library of antibody producing host cells are deposited onto a solid support in a way that each antibody can be identified, e.g. with a plate number and position on the plate, or another identifier that will allow the identification of the host cell culture that produced the antibody.

The antibodies of the invention may be screened for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally involve lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4.degree. C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally involves preparation of protein samples followed by electrophoresis of the protein samples in a polyacrylamide gel (e.g., 8%-20% SDS-PAGE depending on the molecular weight of the antigen), and transfer of the separated protein samples from the polyacrylamide gel to a membrane such as nitrocellulose, PVDF or nylon. Following transfer, the membrane is blocked in blocking solution (e.g., PBS with 3% BSA or non-fat milk), washed in washing buffer (e.g., PBS-Tween 20), and incubated with primary antibody (the antibody of interest) diluted in blocking buffer. After this incubation, the membrane is washed in washing buffer, incubated with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 1251), and after a further wash, the presence of the antigen may be detected. One of skill in the art would be knowledgeable as to the parameters that can be modified to increase the signal detected and to reduce the background noise.

ELISAs involve preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Antibodies of the invention may be screened using immunocytochemistry methods on cells (e.g., mammalian cells, such as CHO cells) transfected with a vector enabling the expression of an antigen or with vector alone using techniques commonly known in the art. Antibodies that bind antigen transfected cells, but not vector-only transfected cells, are antigen specific.

In certain embodiments, however, the assay is an antigen capture assay, and an array or microarray of antibodies may be employed for this purpose. Methods for making and using microarrays of polypeptides are known in the art (see e.g. U.S. Pat. Nos. 6,372,483, 6,352,842, 6,346,416 and 6,242,266).

Inhibitor Assays

In certain embodiments, the assay measures the specific inhibition of an antibody to an interaction between a first compound and a second compound (e.g. two biopolymeric compounds) or specifically inhibits a reaction (e.g. an enzymatic reaction). In the interaction inhibition assay, one interaction substrate, usually a biopolymeric compound such as a protein e.g. a receptor, may be bound to a solid support in a reaction vessel. Antibody is added to the reaction vessel followed by a detectable binding partner for the substrate, usually a biopolymeric compound such as a protein e.g. a radiolabeled ligand for the receptor. After washing the vessel, interaction inhibition may be measured by determining the amount of detectable binding partner present in the vessel. Interaction inhibition occurs when binding of the binding partner is reduced greater than about 20%, greater than about 50%, greater than about 70%, greater than about 80%, or greater than about 90% or 95% or more, as compared to a control assay that does not contain antibody.

In the reaction inhibition assay, an enzyme may be bound to a solid support in a reaction vessel. Antibody is usually added to the reaction vessel followed by a substrate for the enzyme. In many embodiments, the products of the reaction between the enzyme and the substrate are detectable, and, after a certain time, the reaction is usually stopped. After the reaction has been stopped, reaction inhibition may be measured by determining the level of detectable reaction product present in the vessel. Reaction inhibition occurs when the rate of the reaction is reduced greater than about 20%, greater than about 50%, greater than about 70%, greater than about 80%, or greater than about 90% or 95% or more, as compared to a control assay that does not contain antibody.

In Vivo Assays

In certain embodiments the monoclonal antibodies are tested in vivo. In general, the method involves administering a subject monoclonal antibody to an animal model for a disease or condition and determining the effect of the monoclonal antibody on the disease or condition of the model animal. In vivo assays of the invention include controls, where suitable controls include a sample in the absence of the monoclonal antibody. Generally a plurality of assay mixtures is run in parallel with different antibody concentrations to obtain a differential response to the various concentrations. Typically, one of these concentrations serves as a negative control, i.e. at zero concentration or below the level of detection.

A monoclonal antibody of interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Monoclonal antibodies that have therapeutic value that have been identified using the methods and compositions of the invention are termed "therapeutic" antibodies.

Since a hybrid cell expressing an antibody of interest contains immunoglobulin heavy and light chain-encoding nucleic acids, the nucleic acids encoding the monoclonal antibody of interest may be identified if the host cell expressing the monoclonal antibody of interest is identified. As such, the subject nucleic acids may be identified by a variety of methods known to one of skill in the art. Similar methods are used to identify host cell cultures in monoclonal antibody production using hybridoma technology (Harlow et al., *Antibodies: A Laboratory Manual*, First Edition (1988) Cold spring Harbor, N.Y.).

For example, upon identifying a monoclonal antibody of interest, the host cell expressing the antibody of interest may be identified using a "look-up" table which lists, for every antibody sample, the corresponding host cell culture. In certain other embodiments, a look-up table containing antibody library sample identifiers, corresponding expression cassette library sample identifiers and/or host cell identifiers may be used to identify the subject nucleic acids.

Once identified, the nucleic acids encoding a monoclonal antibody of interest may be recovered, characterized and manipulated using techniques familiar to one of skill in the art (Ausubel, et al, Short Protocols in Molecular Biology, 3rd ed., Wiley & Sons, (1995) and Sambrook, et al, Molecular Cloning: A Laboratory Manual, Third Edition, (2001) Cold Spring Harbor, N.Y.).

Antibody Expression

Also provided are several methods of producing a monoclonal antibody of interest. In general these methods involve incubating a host cell containing a nucleic acid encoding a monoclonal antibody of interest under conditions sufficient for production of the antibody.

In some embodiments, the methods of producing a monoclonal antibody of interest involve transferring identified expression cassettes for a monoclonal antibody of interest into a suitable vector, and transferring the recombinant vector into a host cell to provide for expression of the monoclonal antibody. In some embodiments, the subject methods involve transferring at least the variable domain-encoding sequences from the identified heavy and light chains into vectors suitable for their expression in immunoglobulin heavy and light chains. Suitable constant domain-encoding sequences and/or other antibody domain-encoding sequences may be added to the variable domain-encoding sequences at this point. These nucleic acid modifications may also allow for humanization of the subject antibody.

The subject monoclonal antibodies can be produced by any method known in the art for the synthesis of antibodies, in particular, by recombinant expression techniques.

Recombinant expression of a subject monoclonal antibody, or fragment, derivative or analog thereof, usually requires construction of an expression vector containing a polynucleotide that encodes the antibody. Methods which are well known to those skilled in the art can be used to construct expression vectors containing antibody coding sequences and appropriate transcriptional and translational control signals. These methods include, for example, in vitro recombinant DNA techniques and synthetic techniques. As such, the invention provides vectors comprising a nucleotide sequence encoding an antibody molecule of the invention.

The expression vector is transferred to a host cell by conventional techniques and the transfected cells are then cultured to produce a subject antibody. In most embodiments, vectors encoding both the heavy and light chains are co-expressed in the host cell to provide for expression of the entire immunoglobulin molecule.

A variety of host-expression vector systems may be utilized to express a subject monoclonal antibody. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells etc.) harboring recombinant expression constructs containing promoters derived from the genome of mammalian cells (e.g., metallothionein promoter) or from mammalian viruses (e.g., the adenovirus late promoter; the vaccinia virus 7.5K promoter). In many embodiments, bacterial cells such as *Escherichia coli*, and eukaryotic cells are used for the expression of entire recombinant antibody molecules. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express antibodies. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993) and Morgan and Anderson, Ann. Rev. Biochem. 62:191-217 (1993); TIB TECH 11(5):155-215 (1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981).

The host cell may be co-transfected with two expression vectors of the invention, the first vector encoding a heavy chain derived polypeptide and the second vector encoding a light chain derived polypeptide. The two vectors may contain different selectable markers and origins of replication, which enable equal expression of heavy and light chain polypeptides. Alternatively, a single vector may be used which encodes, and is capable of expressing, both heavy and light chain polypeptides.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Utility

Also provided is a method for modulating or treating at least one antigen-related disease, in a cell, tissue, organ, animal, or patient, as known in the art or as described herein, using at least one antibody of the present invention, e.g., administering or contacting the cell, tissue, organ, animal, or patient with a therapeutic effective amount of antibody. The present invention also provides a method for modulating or treating at least one antigen related disease, in a cell, tissue, organ, animal, or patient including, but not limited to, at least one of obesity, an immune related disease, a cardiovascular disease, an infectious disease, a malignant disease or a neurologic disease.

Typically, treatment of pathologic conditions is effected by administering an effective amount or dosage of at least one antibody composition that total, on average, a range from at least about 0.01 to 500 milligrams of at least one antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 ng/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

A subject antibody can, in certain embodiments also be used in diagnostics where the antibody is conjugated to a detectable markers or used as primary antibodies with secondary antibodies that are conjugated to detectable markers. Detectable markers, include radioactive and non-radioactive labels and are well-known to those with skill in the art. Common non-radioactive labels include detectable enzymes such as horseradish peroxidase, alkaline phosphatase and fluorescent molecules. Fluorescent molecules absorb light at one wavelength and emit it at another, thus allowing visualization with, e.g., a fluorescent microscope. Spectrophotometers, fluorescence microscopes, fluorescent plate readers and flow sorters are well-known and are often used to detect specific molecules which have been made fluorescent by coupling them covalently to a fluorescent dye. Fluorochromes such as green fluorescent protein, red shifted mutants of green fluorescent protein, amino coumarin acetic acid (AMCA), fluorescein isothiocyanate (FITC), tetramethylchodamine isothiocyanate (TRITC), Texas Red, Cy3.0 and Cy5.0 are examples of useful labels.

The molecules can be used in cell isolation strategies such as fluorescence-activated cell sorting (FACS) if fluorescent markers are used, In fluorescence-activated cell sorting, cells tagged with fluorescent molecules are sorted electronically on a flow cytometer such as a Becton-Dickinson (San Jose, Calif.) FACS IV cytometer or equivalent instrument. The fluorescent molecules are antibodies that recognize specific cell surface antigens. The antibodies are conjugated to fluorescent markers such as fluorescein isothiocyanate (FITC) or Phycoerythrin (PE).

EXAMPLES

The following examples are provided in order to demonstrate and further illustrate certain embodiments and aspects of the present invention and are not to be construed as limiting the scope thereof.

Example 1

Summary

Briefly, a chicken is engineered to produce antibody containing a human framework with biophysical properties and that is easily manufactured and has optimal pharmacological properties. The immunoglobulin genes of the engineered chicken will have an array of 20 synthetic pseudogenes with the identical framework region and CDRs composed of random sequences of serine, tyrosine, alanine and aspartate to generate antigen-specific, high-affinity antibodies. This line of chickens will be immunized and monoclonal antibodies will be recovered.

Gene conversion of an array of VL pseudogenes where all pseudogenes have an identical framework region and the CDRs are composed of random arrays of serine, tyrosine, alanine and aspartate will be demonstrated using DT40 cells from a virally transformed chicken pre-B cell line that continues to diversify the light chain by gene conversion in vitro. Furthermore, DT40 cells undergo high rates of homologous recombination which provides a straightforward route for replacement of the chicken functional variable region with a recombinant variable region.

Knock-in targeting vectors to replace the array of chicken light chain V regions in DT40 cells with a synthetic array derived from a single human framework region and CDRs comprised of serine, tyrosine, alanine and aspartate will be created. Gene conversion of the synthetic CDRs in a single human framework will be demonstrated in DT40 cells.

An array of synthetic human V regions will be inserted into the chicken IgL and IgH loci of primordial germ cells (PGCs). The genetically modified PGCs will be used to create a line of birds from which human antibodies can be obtained following immunization. These birds will be the first transgenic animals yielding engineered human antibodies with predictable manufacturing attributes and pharmacological properties.

The $V_\kappa 3$ framework sequence will be used because it has the highest solubility, exists as a monomer, and is thermodynamically stable. The $V_H 3$ framework sequence will be used for the same reasons and because the $V_H 3$ framework has been shown to be well expressed.

Example 2

Functional V and the Pseudogene Array

A functional V (i.e., V region) was obtained by extracting a consensus sequence for the framework, CDR1 and CDR2 of the human $V_\kappa 3$ sequences listed the VBase database. Since no consensus can be derived for CDR3 of $V_\kappa 3$, the humIGKV096 sequence from VBase was used; this $V_{K}3$ sequence was confirmed in genomic DNA as well as in productive rearrangements. The pseudogenes were designed to use the consensus sequence of $V_\kappa 3$ as the framework region and random arrays of tyrosine (Y), serine (S), and tryptophan (W) in CDR1, CDR2 and CDR3. These sequences are shown below in Table 1.

The CDR regions of the pseudogene array were constructed from only 3 amino acids: tyrosine (Y), serine (S), and tryptophan (W) in proportions of 40/50/10%, respectively. In this strategy, tyrosine and tryptophan are predicted to be the primary antigen-contact residues, while serine provides appropriate spacing within the binding pocket. The array is designed to allow a Y or W to appear in any position of any CDR and to collectively provide a sufficient number of alternatively ordered sequences to generate any possible sequence efficiently through gene conversion. This design assumes that diversity will be generated from the synthetic array using the same gene conversion process that is used to generate a repertoire from the pseudogene array in wild-type chickens.

The performance of this array was tested in silico, by creating a panel of mock "antigen-selected" CDR sequences comprised of Y, S and W residues. The approximate composition of the array (listed in Table 1) was 40% tyrosine, 50% serine, and 10% tryptophan, a distribution that is thought to be optimal in vitro. The simulated amino acid sequence (SAAS) of CDR1 (or CDR3 since both have 6 positions) was created using a random number generator and assigning a value of 0 to 0.4 to tyrosine, >0.4 to 0.9 to serine

TABLE 1

Sequence of tyrosine (Y), serine (S), and tryptophan (W) in CDR1, CDR2 and CDR3 in the functional VK3 derived gene and in the pseudo-V (PSI) genes.

| | CDR1 | | CDR2 | CDR3 | |
|---|---|---|---|---|---|
| VK3 consensus | QSVSSN | (SEQ ID NO: 7) | GAS | QQYNNW | (SEQ ID NO: 28) |
| PSI-1 | YSSYSS | (SEQ ID NO: 8) | YSS | YSSYSS | (SEQ ID NO: 29) |
| PSI-2 | SYSSYS | (SEQ ID NO: 9) | SYS | SYSSYS | (SEQ ID NO: 30) |
| PSI-3 | SSYSSY | (SEQ ID NO: 10) | SSY | SSYSSY | (SEQ ID NO: 31) |
| PSI-4 | YSYSYS | (SEQ ID NO: 11) | SSS | YSYSYS | (SEQ ID NO: 32) |
| PSI-5 | SYSYSY | (SEQ ID NO: 12) | SSS | SYSYSY | (SEQ ID NO: 33) |
| PSI-6 | YSSSSY | (SEQ ID NO: 13) | SSS | YSSSSY | (SEQ ID NO: 34) |
| PSI-7 | YYSSSS | (SEQ ID NO: 14) | YSS | YYSSSS | (SEQ ID NO: 35) |
| PSI-8 | SYYSSS | (SEQ ID NO: 15) | SYS | SYYSSS | (SEQ ID NO: 36) |
| PSI-9 | SSYYSS | (SEQ ID NO: 16) | SSY | SSYYSS | (SEQ ID NO: 37) |
| PSI-10 | SSSYYS | (SEQ ID NO: 17) | SSS | SSSYYS | (SEQ ID NO: 38) |
| PSI-11 | SSSSYY | (SEQ ID NO: 18) | SSS | SSSSYY | (SEQ ID NO: 39) |
| PSI-12 | WSYSSS | (SEQ ID NO: 19) | SSS | WSYSSS | (SEQ ID NO: 40) |
| PSI-13 | SWSYSS | (SEQ ID NO: 20) | YSS | SWSYSS | (SEQ ID NO: 41) |
| PSI-14 | SSWSYS | (SEQ ID NO: 21) | SYS | SSWSYS | (SEQ ID NO: 42) |
| PSI-15 | SSSWSY | (SEQ ID NO: 22) | SSY | SSSWSY | (SEQ ID NO: 43) |
| PSI-16 | YSSSWS | (SEQ ID NO: 23) | SSS | YSSSWS | (SEQ ID NO: 44) |
| PSI-17 | SYSSSW | (SEQ ID NO: 24) | SSS | SYSSSW | (SEQ ID NO: 45) |
| PSI-18 | WYWYWY | (SEQ ID NO: 25) | YSS | WYVVYVVY | (SEQ ID NO: 46) |
| PSI-19 | YWYWYW | (SEQ ID NO: 26) | SYS | YWYVVYVV | (SEQ ID NO: 47) |
| PSI-20 | SSSSSS | (SEQ ID NO: 27) | SSY | SSSSSS | (SEQ ID NO: 48) | and >0.9 to 1 to tryptophan. The output of this simulation for CDR1 (or CDR3) is shown in Table 2.

TABLE 2

The simulated amino acid sequence (SAAS) of CDR1 (or CDR3) and the gene conversion (GC) events needed to generate the predicted sequence from the pseudogene (PSI) array in Table 1.

| CDR Position | 1 | 2 | 3 | 4 | 5 | 6 | # GC events | PSI used |
|---|---|---|---|---|---|---|---|---|
| SAAS-1 | S | Y | S | S | S | S | 2 | p 2, 7 |
| SAAS-2 | S | S | S | Y | W | S | 2 | p 10, 16 |
| SAAS-3 | S | S | Y | Y | S | Y | 2 | p 9, 6 |
| SAAS-4 | W | S | S | Y | Y | W | 3 | p 12, 10, 17 |
| SAAS-5 | S | W | Y | W | S | S | 3 | p 13, 19, 7 |
| SAAS-6 | Y | S | W | W | S | S | 4 | p 4, 14, 15, 12 |
| SAAS-7 | S | Y | W | Y | S | S | 3 | p 2, 14, 9 |
| SAAS-8 | S | Y | S | Y | Y | S | 2 | p 5, 10 |
| SAAS-9 | S | S | Y | Y | W | Y | 2 | p 9, 18 |
| SAAS-10 | Y | Y | S | Y | Y | Y | 3 | p 7, 5, 11 |
| SAAS-11 | Y | Y | Y | Y | Y | S | 3 | p 7, 9, 10 |
| SAAS-12 | Y | W | W | W | W | Y | 3 | p 18, 19, 18 |
| SAAS-13 | W | S | Y | S | S | Y | 2 | p 12, 6 |
| SAAS-14 | W | S | S | Y | Y | Y | 2 | p 12, 3 |
| SAAS-15 | S | Y | Y | W | W | S | 3 | p 8, 15.16 |
| Average | | | | | | | 2.6 | |

The minimum number of gene conversions that would be required to achieve the simulated amino acid sequences in Table 2 and the PSI that could be used to create the SAAS was manually evaluated and are shown in the column "GC events". Generally we were able to create any SAAS with only 2 or 3 gene conversion-like events, with an average of 2.6. Since the published estimates of gene conversion frequency ranges from 3-6 independent events per V gene, the pseudogene array should be able to produce sufficient sequence and functional diversity to generate highly specific clones to any antigenic sequence.

Example 3

Gene Targeting Constructs

Modification of the genome will be done in two steps. First a gene targeting vector will be introduced into the chicken DT-40 cells to remove the entire array of endogenous chicken light chain pseudo V genes (around 20 Kb sequences) as well as the chicken functional V region (including leader, VJ and corresponding intronic sequences). The schematic design of the targeting vector is illustrated in FIG. 1.

Figure 2:
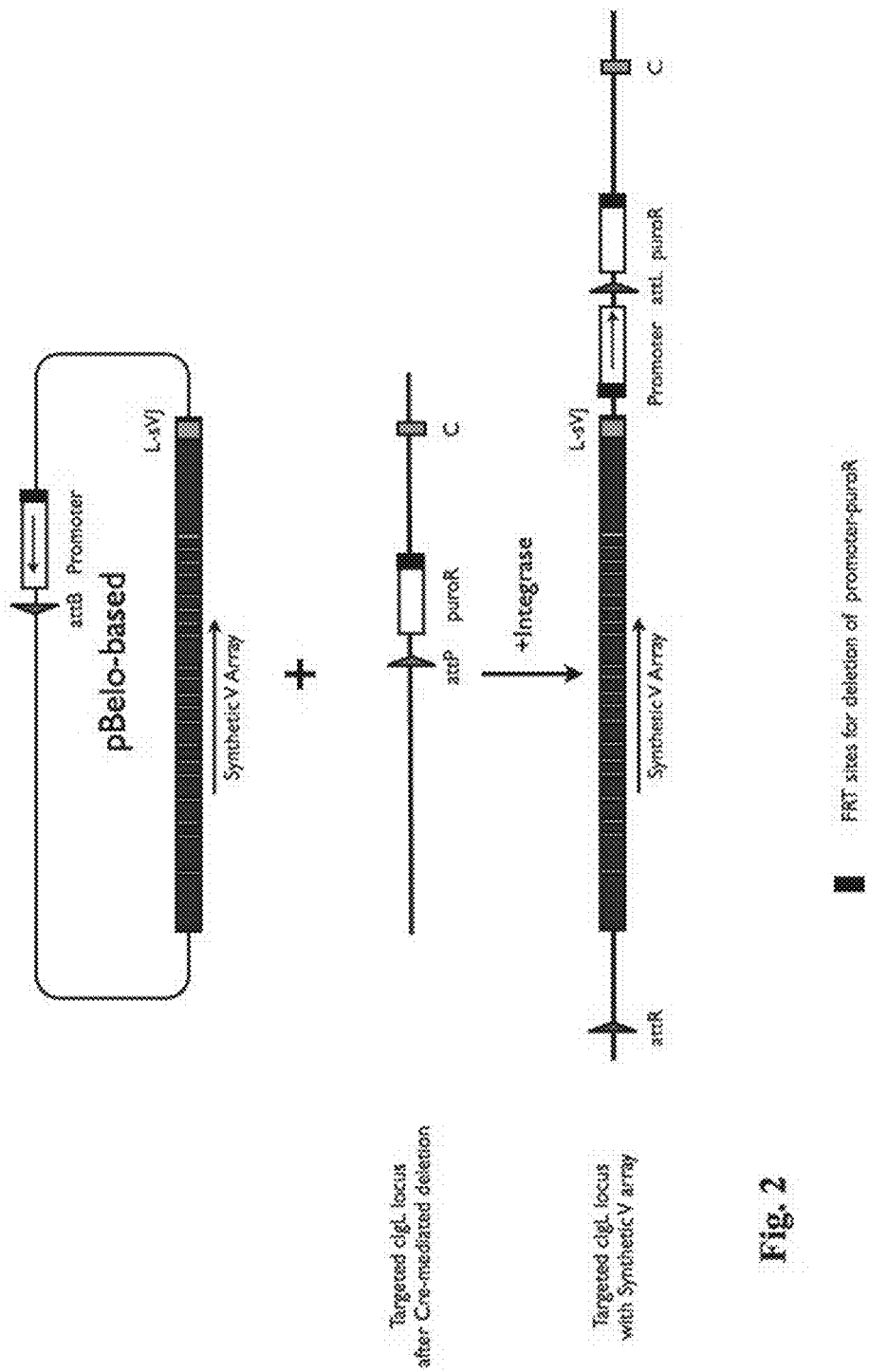
FIG. 2 schematically illustrates a strategy for adding a synthetic array of variable region-encoding pseudogenes to a chicken immunoglobulin light chain locus after deletion of the endogenous chicken immunoglobulin light chain gene.

Sequences upstream of the pseudo V25 will be used as the 5' homologous region and sequences downstream of J in the J-C intron can be used as the 3' homologous region to facilitate the targeting by homologous recombination. A loxP flanked neoR cassette driven by the β-actin promoter will be used for selection which can then be removed in the targeted cells by cre-mediated recombination. In addition, an attP site and a promoterless puroR (with a FRT sequence at 3' end) will be included in the targeting vector (see description below). This facilitates the easy integration of other arrays of synthetic Vs if necessary. The resulting targeted locus will have the entire chicken pseudo V and functional V array removed. In the second step, a synthetic V array (with both synthetic pseudo Vs and functional $V_\kappa 3$ shown as L-sVJ in FIG. 2) in a replacement vector with an attB site and a promoter (with a FRT sequence at 5' end) will be inserted to the pre-targeted locus at the attP site via a phage phiC31 integrase-mediated site-specific recombination (FIG. 2). The correct integration event will bring the promoter and the promoterless puroR together to allow selection with puro. This will further enrich the correct integration at the pre-introduced attP site to almost 100% efficiency against integrations at pseudo attP sites present in the chicken genome. Again the promoter-puroR sequence can be removed via FRT if necessary.

Figure 3:
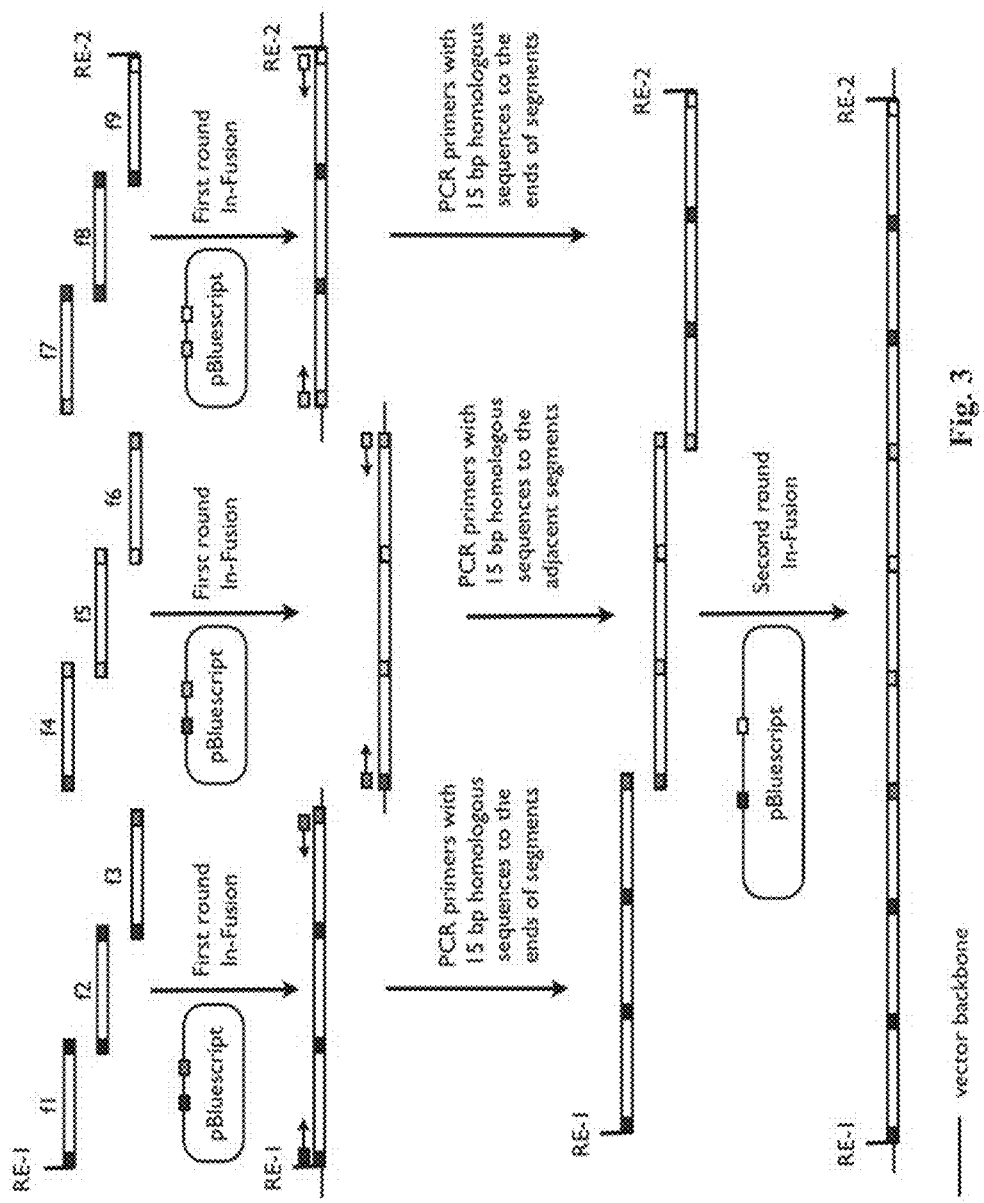
FIG. 3 schematically illustrates a strategy for constructing an array of variable region-encoding pseudogenes.
Figure 4:
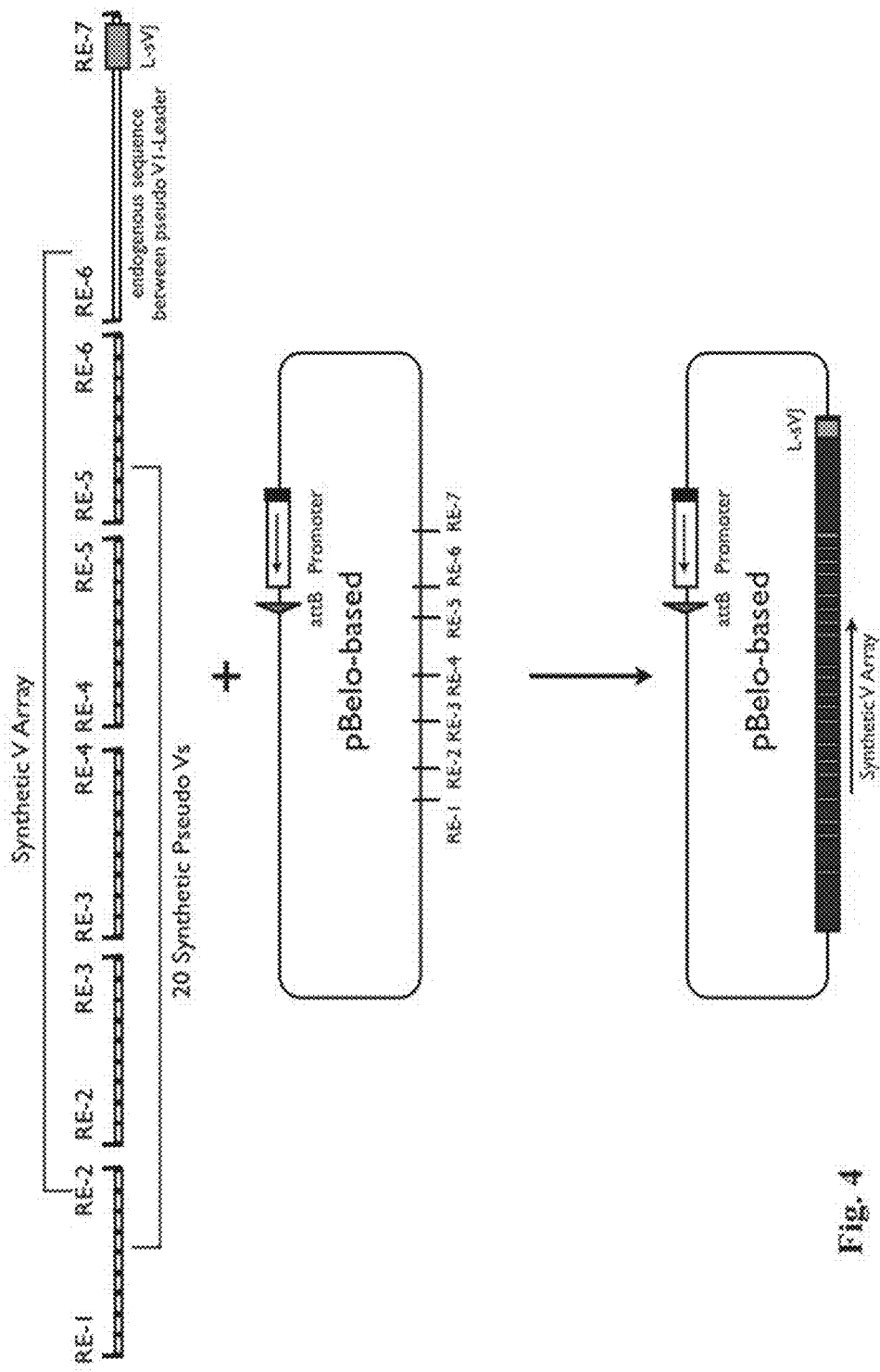
FIG. 4 schematically illustrates a strategy for constructing a vector for inserting an array of variable region-encoding pseudogenes.

The assembly of the synthetic V array is illustrated in FIG. 3 and FIG. 4. Specifically, the In-Fusion technology developed by Clontech will be used to generate subfragments of synthetic Vs for downstream cloning into the final vector. The In-Fusion technology can efficiently "fuse" DNA fragments with a 15-bp overlap of homologous sequence at the ends. The 15 bp homologous ends can be added to the end of gene-specific PCR primers. This technology has been used to efficiently assemble four or more pieces of DNA seamlessly. To reconstitute the synthetic pseudo V array, 39 segments (20 synthetic pseudo Vs and 19 inter-pseudo V sequences derived from endogenous chicken IgL sequences) spanning about 25 Kb will be joined together. Synthetic pseudo V genes will be obtained by gene synthesis. Inter-pseudo V sequences will be obtained by PCR from BAC DNA. A BAC clone (CH261-29C12) containing the entire cIgL locus will be obtained from the Children's Hospital Oakland Research Institute (CHORI). In the process 15-bp homologous ends will be added to the ends of each segment. Initially, 3 segments will be assembled together by In-Fusion. Each segment contains a 15 bp sequence that is homologous (color-coded) to the adjacent segments or vectors. A modified pBluescript-based intermediate vector will be used as the linearized vector DNA for In-Fusion. After the first round of In-Fusion, there are 13 intermediate segments. These 13 segments will go through a second round of In-Fusion to yield 5 final segments which will contain up to 9 starting segments each.

Unique restriction sites will be added at the indicated locations of the final segments to facilitate the assembly of the entire synthetic pseudo V locus via conventional restriction site-mediated cloning. A pBeloBAC-based vector will be modified to include attB and the Promoter, and 7 unique restriction sites (RE-1 to RE-7) to allow the final assembly of the synthetic V array. A DNA fragment containing the endogenous chicken sequence between pseudo V1-Leader and sequence of leader-Synthetic human VJ framework (L-sVJ in FIG. 4) will be cloned into the vector to reconstruct the entire VL locus.

Since the frequency of gene conversion can be sensitive to transcription of nearby loci we have designed the constructs with Lox or FRT sites flanking the selectable marker to facilitate its removal. To excise the gene encoding resistance to neomycin, the clones will be transfected with a plasmid expressing Cre-recombinase (Vector Biolabs) and to excise the gene encoding resistance to puromycin, and the clones will be transfected with a plasmid expressing Flipase (Invitrogen). Cells will then be singly seeded to obtain clones without the selectable marker. Once these clones are apparent (usually in 5-7 days), we will use Southern analysis to verify that the antibiotic resistance gene has been excised. We will then add 1.5 ng/ml trichostatin A to the cultures to enhance gene conversion. During the next 4 weeks, we will monitor reversion to the sIgM+ phenotype and assess the contribution of chicken pseudo V regions to the human V sequence.

Example 4

Culture and Transfection of DT40 Cells

DT40 cells are grown in DMEM supplemented with 10% tryptose phosphate broth, 55 µM beta-mercaptoethanol, 2 mM L-glutamine, 10% FBS and 2% chicken serum. Cells are seeded at $2.5 \times 10^5$ cells/ml and are split at 2 to 3 day intervals. Care is taken to prevent the cultures from becoming too dense.

For transfection $5 \times 10^6$ cells in logarithmic phase growth are collected, washed with PBS, pelleted and re-suspended in 100 µl Amaxa V-buffer. Five µg of linearized DNA is added, the suspension is transferred to a cuvette and electroporated using an exponential decay pulse of 550V and 25 µF. Immediately after electroporation the cells are put in 500 µl of prewarmed medium in an 1.5 ml Eppendorf tube and placed at 37° C. After 20 minutes, the cells are resuspended in 40 mls of medium and aliquots of 1000 are deposited into four 96-well plates. The day after transfection an equal volume (100 µl) of medium containing the antibiotic being used for selection (e.g puromycin in a 2× concentration of 1 mg/ml) is added for a final puromycin concentration of 0.5 mg/ml. Within 5 to 7 days, colonies grow to about 2 mm in diameter and are transferred to 24-well plates. Colonies are then expanded using the same culture conditions that are described above.

Stably transfected clones will be analyzed by PCR to determine targeting and targeting will be confirmed in prospective clones by Southern analysis. We will identify at least two clones by Southern analysis for each of the genetic modifications.

Example 5

Evaluation of Gene Conversion Using the sIgM Reversion Assay

The rate of gene conversion will be monitored by an sIgM+ reversion assay (Yang e al., J. Exp. Med. 203: 2919-2928, 2006). In this system, the frameshift variant DT40-CL18, which has a single base insertion at position 128 in the VL gene, prevents the light chain from pairing with endogenous heavy chain, and thus the cells are surface IgM− (Yang et al, 2006). When the frameshift mutation is reverted due to a gene conversion event, the cells become sIgM+, a phenotype that is readily identified by Fluorescence Activated Cell Sorting (FACS). Four weeks after starting a culture from the DT40-CL18 frameshift variant, approximately 1.5% of the cells will be sIgM+. These clones are then recovered and the V regions sequenced to fully document diversification of the functional V.

In this application, the functional $V_\kappa 3$ gene is a consensus sequence and therefore, the CDRs are composed of tryptophan, glycine, valine, glutamine and asparagine in addition to serine, alanine and tyrosine. Accumulation of the four amino acids in the synthetic pseudo Vs will be the metric for gene conversion.

To use the sIgM reversion assay in this application, the human functional V region will be engineered to contain an amber stop codon in CDR1. Hence, both wild type and mutant versions of the transgene will be alternatively inserted into the introduced attP site in the genome of DT40 cells. The wild type version will provide evidence that the functional light chain is capable of pairing with the endogenous heavy chain to reconstitute IgM expression. Since both heavy and light chain constant regions are of chicken origin, it is likely that normal pairing will occur, but there is a possibility of interference between the human and chicken V regions. If that is the case, we will not be able to take advantage of the sIgM+ reversion assay and will rely exclusively on sequencing analysis for evaluation of gene conversion events. However, complete antibodies are assembled when murine variable regions are spliced onto chicken constant regions lending credence to our supposition that chimeric human-chicken light chains will pair with chicken heavy chains. Furthermore, $V_\kappa 3$ is about 70% homologous to chicken functional Vs and this level of homology is expected to facilitate productive pairing.

At the end of the four week culture period, the cells expressing the mutant version of the transgene will be stained with a rabbit anti-chicken Ig (Sigma) and single sIgM+ cells will be sorted by FACS into 96 well plates. These data will provide the first indication that gene conversion has occurred and we anticipate that approximately 1.5% of the cells will be sIgM+ (Yang et al, 2006). The cells will be grown for 5-7 days and IgM mRNA will be prepared from each of the wells. The resulting cDNA will be amplified with a 5' leader peptide primer and a 3' CL primer. Both primers are of chicken origin and will therefore amplify VL regardless of the extent of gene conversion. Amplicons will be cloned into the TOPO TA cloning vector (Invitrogen). Plasmid DNA from *E. coli* transformant colonies will be prepared from each well and the cloned insert will be sequenced. Sequences will be analyzed relative to the original CDRs and the accumulation of tyrosine, serine and tryptophan will be used as an index of gene conversion.

Example 6

Knock-Out Vectors and Transfection of the Same in DT40 Cells

The data presented in the following examples show that human Ig light chain transgene comprised of a single framework region and an array of upstream human synthetic pseudogenes can be inserted into the chicken light chain locus of the chicken B cell line DT40. Gene conversion diversifies the synthetic CDRs in chicken B cells.

The replacement of the chicken light chain locus with human V regions was done in two steps, as described above: knockout of the chIgL locus and placement of an attP site in the locus, followed by knock-in of the human V regions using integrase. The knockout vector was designed to delete the V, J and C regions (FIG. 5), leaving behind the chicken pseudogenes, which would not be predicted to interfere with gene conversion since sequence homology to the human V is low (only small stretches of weak homology in framework region 2).

5' and 3' homology arms for the targeting vector were prepared by PCR amplification of genomic DNA and assembled with the puromycin, EGFP and promoterless neo selectable cassette. The EGFP marker is useful for identifying and tracking transfected cells and colonies, especially in the case of gonocytes because the feeder layer that the cells are grown on sometimes makes visualization of small colonies difficult. In addition, EGFP facilitates the screening for germline transmission of knockout or knock-in gonocytes by shining UV light onto chicks and assessing green fluorescence. The puromycin gene is used for selection of the knockout clones, and the promoterless neo gene will be used later for selection of integrase-mediated insertion of the array of pseudogenes. An attP site was placed in front of the neo gene for recombination by ΦC31 integrase. loxP sites were included for later removal of the selectable markers by Cre recombinase.

Figure 6:
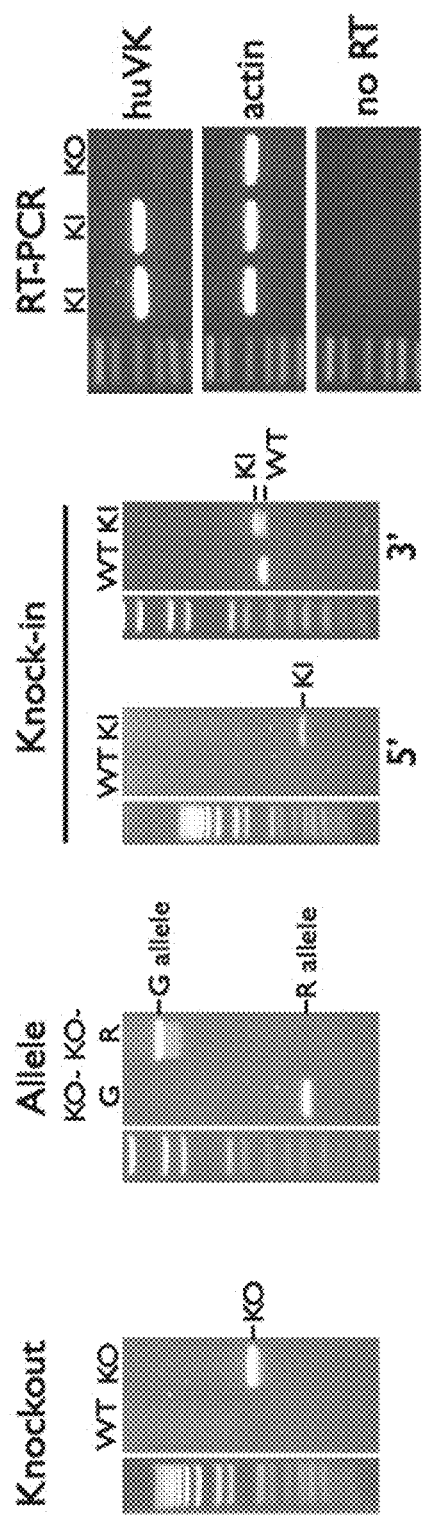
FIG. 6 show the results of PCR analysis of chicken IgL knockout and knock-in clones.

The knockout vector transfected into wild type DT40 cells, puromycin-resistant clones were selected and clones that had integrated the vector by homologous recombination were screened for, thereby knocking out the light chain. Of the two alleles of the light chain gene in DT40, one is in germline configuration and is not expressed, whereas the other has undergone VJ rearrangement to express the light chain gene. The rearranged allele may be knocked out because it eliminates expression of the endogenous light chain, leading to surface IgM-negative cells and simplifying downstream analysis. The germline allele cannot rearrange because RAG-1 is not expressed. Of the 117 clones screened, 8 clones had a knockout of the rearranged allele and 10 had a knockout of the germline allele, for an overall frequency of about 15% targeting, an expected frequency for DT40. FIG. 6 shows an example of results of a screen.

The left panel of FIG. 6 shows results obtained from a knockout. One primer is in the genomic flanking region 5' of the targeting vector (actgtgctgcaggtggctatg; SEQ ID NO: 53), and the other primer is in the selectable marker cassette (atacgatgttccagattacgctt; SEQ ID NO:54). The second panel of FIG. 6 shows allele-specific PCR. Both primers are in the chicken light chain locus (forward primer GCGCTGACTCAGCCGTCCTC (SEQ ID NO:55); reverse primer gagacgaggtcagcgactcac (SEQ ID NO:56)) and produce a smaller product from the rearranged allele (R allele) because the VJ intron has been deleted from that allele; the germline allele (G allele) contains the intron and produces a larger fragment. In the knockout of the germline allele (KO-G) only the R allele is detected. In the knockout of the rearranged allele (KO-R) only the G allele is detected. Third set of panels in FIG. 6 shows results obtained for the knock-in. The 5' assay detects the β-actin-neo fusion on the 5' side of integration (forward primer ctctgctaaccatgttcatgccttc (SEQ ID NO:57); reverse primer AGTGACAACGTCGAGCACAGCT (SEQ ID NO:58)). The 3' assay employs two primers in the light chain spanning the attR site (forward primer cgcacacgtataacatccatgaa (SEQ ID NO:59); reverse primer gtgtgagatgcagacagcacgc (SEQ ID NO:60)). In knock-in samples, both the wild type allele and knock-in allele are detected, whereas in wild type samples only the wild type fragment is observed. The fourth panel of FIG. 6 shows RT-PCR results that show expression of the huVK-chCL chimeric light chain in two knock-in DT40 clones (KI) (huVK reaction: forward primer ATGGAAGCCCCAGCTCAGCTTC (SEQ ID NO:61); reverse primer caggtagctgctggccatatac (SEQ ID NO:62); B-actin reaction forward primer aacaccccagccatgtatgta (SEQ ID NO:63); B-actin reaction reverse primer tttcattgtgctaggtgcca (SEQ ID NO:64)). Control sample was the parental knockout (KO).

Example 7

Knock-in Vectors and Transfection of the Same in DT40 Cells

The functional V and pseudogene array was assembled from several chicken and human Ig sequences (FIG. 7). The vector includes a functional, rearranged human V kappa gene (huVK), a chicken light chain constant region, an array of synthetic VK pseudogenes (SynVK) and chicken introns and regulatory sequences for proper expression of the light chain. The functional VK fulfills several criteria, both for downstream manufacturing capability and in order to support B cell development in the chicken. The functional VK and VH used should express at high levels, fold into the proper structure, pair with each other efficiently to form a functional antibody molecule, and not recognize any chicken epitopes which would lead to self-reactive B cells in the chicken.

To select a functional pair of human VK and VH genes for insertion, a number of rearranged, functional human Vs were cloned from human B cell DNA. 16 VK and 16 VH genes were then expressed in combinations to find a pair that would form a functional antibody that expresses at high levels. The selected VK sequence, clone E6, was identical to the germline gene $V_K3-15$ except for 3 amino acid changes in framework region 1. The SynVK pseudogene array was designed to have framework regions identical to huVK E6, and CDRs that contain tyrosine and tryptophan. The SynVK genes were synthesized and assembled into an array of 12 pseudogenes. The functional human VK was synthesized with chicken intron sequences and was then cloned with the chicken light chain promoter, constant region and J-C intron. The resulting knock-in locus will express a chimeric light chain consisting of fully human V region spliced to the chicken light chain constant region, using chicken non-coding, regulatory sequences. Finally, for insertion of the vector into the knockout allele we added an attB site and β-actin promoter, and a loxP site was included for eventual excision of the selectable markers and plasmid backbone. The knock-in strategy is illustrated in FIG. 7.

The SynVK insertion vector was designed to enable a simple surface IgM (sIgM) reversion assay for gene conversion (Buerstedde, Reynaud et al. 1990. Light chain gene conversion continues at high rate in an ALV-induced cell line Embo J 1990 vol. 9 (3) pp. 921-7). A stop codon was introduced into the CDR1 of the "functional" expressed human V region, so that full-length light chain will not be expressed. With no light chain present, the DT40 heavy chain will not traffic to the cell surface and the knock-in cells will be sIgM negative. Gene conversion in CDR1 by the SynVK pseudogenes, which do not contain the stop codon, will repair the light chain sequence and restore its full-length open reading frame. The light chain can then bind to the heavy chain to form the full IgM complex, and the cells will become sIgM-positive. The DT40 knock-in clones can be stained for sIgM expression with a mouse anti-chicken IgM antibody (Southern Biotechnology Associates) and sorted for the sIgM-positive cells by flow cytometry to obtain a pure population of gene converted cells for detailed analysis of the gene conversion at the sequence level. A version of the vector with a fully wild type E6 VK region was also made to verify that the chimeric light chain (human V region+chicken C region) is expressed well and can pair with the DT40 heavy chain; goat anti-human kappa antibodies verified the expression of the human variable region on the surface of transfected DT40.

The SynVK insertion vector was co-transfected with a CMV-integrase expression construct into IgL knockout DT40 cells. Both constructs were introduced as circular, supercoiled DNAs. The knockout cells were expected to be sensitive to G418 selection (neomycin) because the neo gene in the knockout allele lacks a promoter, and only after insertion of the SynVK vector, linking the β-actin promoter to the neo gene, would G418 resistance be induced. After transfection of the SynVK vector, cells were selected for insertion in 4 or 6 mg/ml G418 (a relatively high level of drug selection was required because of some background neo-resistance observed in the knockout cells). Colonies were obtained, and two clones out of eight were found to contain the knock-in, using PCR assays for the 5' and 3' sides of the insertion and for the human VK functional gene. FIG. 2 shows PCR results for one of the clones.

Example 8

Demonstration of Gene Conversion of the Synthetic V Regions in DT40 Cells

Light chain knock-in DT40 clones were propagated for several weeks after transfection to allow time for the accumulation of gene conversion events leading to repair of the stop codon and concurrent insertion of tyrosine and tryptophan in CDR1. Cells were sampled at several timepoints and stained for sIgM expression using the mouse anti-chicken IgM antibody. In knock-in clones about two weeks post-transfection, few if any cells expressed sIgM. At 29-41 days post-transfection, a small population (0.2%) of sIgM-positive cells was observed which allowed us to sort cells by FACS for PCR and sequence analysis. Cell lines with an early version of the knock-in construct containing only two pseudogenes (2-SynVK) were analyzed, as well as the version with 12 pseudogenes (12-SynVK).

Genomic DNA was prepared from sorted sIgM+ cells and the functional huVK gene was amplified by PCR using primers in the human VK leader sequence and in the intron downstream of the huVK. PCR products were cloned and single colonies were picked for minipreps and sequencing. Good quality sequence was obtained from about 350 PCR clones. Clear gene conversion that could be unequivocally assigned to a pseudogene donor was observed in 86 clones with 2-SynVK, and 157 clones for 12-SynVK (FIG. 8). Each gene conversion event created a synthetic CDR1 in the functional V containing either tyrosine or tryptophan. Since repair of the stop codon in CDR1 was selected, it follows that many of the gene conversion was observed only in CDR1. In 4 sequences, gene conversion was also observed in CDR2, likely the result of a single, long gene conversion event because the same pseudogene that converted CDR1 also converted CDR2 in each case. Several sequences contained clear gene conversion, but it was impossible to assign a specific pseudogene donor; these sequences could be the result of two overlapping gene conversion events, or a short aborted gene conversion by a single pseudogene. No evidence for gene conversion by a chicken VL pseudogene was observed; all of the gene conversion tracts were derived from the SynVK pseudogene pool. Some point mutations were also observed, which may have been introduced by DT40 or by Taq polymerase errors. However, one sequence had repaired the stop codon by a point mutation, which is likely a DT40-derived mutation because it was selected for sIgM expression.

In both 2-SynVK and 12-SynVK containing cells, all of the SynV pseudogenes participated in gene conversion, except for pseudogene SynVK9 (FIG. 8). With 2-SynVK, the proximal pseudogene was utilized about 9 times more than the distal pseudogene. The two pseudogenes are also in different orientations relative to the functional VK, the proximal pseudogene being in reverse orientation, which raised the question of whether proximity or orientation were more important in determining the efficiency of a pseudogene to participate in gene conversion. In the 12-SynVK cells, proximity to the functional VK did not seem to influence the frequency of gene conversion, as distal pseudogenes and proximal pseudogenes were used at similar frequencies. Thus orientation may be more important than proximity, with a reverse orientation being more efficient.

Figures 8A, 8B:
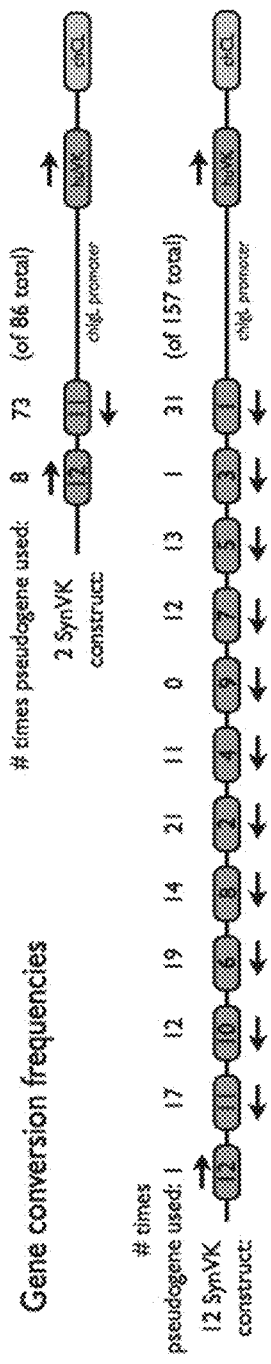
FIGS. 8A and 8B illustrates examples of gene conversion events for CDR1. SEQ ID NOS: 1-6.

The 2-SynVK and 12-SynVK containing constructs are diagrammed in FIG. 8A, showing the numbered SynVK pseudogenes, the functional huVK gene, and the chicken constant region. The pseudogenes were numbered prior to cloning in the array, arbitrarily, and they were not assembled in numerical order. The orientation of the SynVK and huVK are indicated with arrows above or below. The number of times each pseudogene was used in gene conversion is indicated. The total number of gene conversion events is slightly higher because some of the observed gene conversion events could not be assigned to a specific pseudogene. FIG. 8B shows examples of gene conversion events. The CDR1 sequence of the "functional" huVK is shown (Input). The stop codon underlined. Sequences obtained from surface IgM+DT40 are shown below, with the SynVK pseudogene that was used in gene conversion indicated to the right. Tyrosine and tryptophan accumulated in all positions of CDR1. Dashes indicate sequence identity with the input sequence.

Pseudogene SynVK9 had no gene conversion and SynVK3 had only one event. These two pseudogenes insert a bulky residue (tyrosine or tryptophan) at the third codon in CDR1, whereas all of the other pseudogenes insert the wild type valine residue in that position. In this artificial DT40 system with its specific heavy chain, it is possible that a light chain with a bulky residue in that position inactivates that antibody, making it impossible to recover sIgM-positive revertants with gene conversion by these pseudogenes.

These results discussed above demonstrate gene conversion of a human VK region in chicken B cells, creating synthetic CDRs containing tyrosine and tryptophan.

Example 9

Identification of Optimal Human VH and VL Frameworks cDNA was prepared from normal human peripheral blood lymphocytes and PCR amplified with VH3 and $V_K3$ specific primer pairs. The $V_H3$ primers were 5' GGCTGCGATCGC-CATGGAGTTTGGGCTKAGCTGG 3' forward (SEQ ID NO: 49) 5' ATGCGTTTAAACTTTACCCGGAGACA-GGGAGAGG 3' reverse (SEQ ID NO: 50). This primer pair amplified a 1.5 kb DNA fragment corresponding to full heavy chain of the $V_H3$/IgG1 isotype.

The $V_K3$ primers were: 5' GGCTGCGATCGCCATG-GAACCATGGAAGCCCCAGCAC 3' forward (SEQ ID NO: 51) and 5' GGGGGTTTAAACACACTCTCCCCTGT-TGAAGCTCT 3' reverse (SEQ ID NO: 52). This primer pair amplified a 700 bp DNA fragment corresponding to the full light chain of the $V_K3/C_K$ isotype.

Amplicons were cloned directly into the expression vector pF4a (Promega) and verified to have functional coding sequence. Thirty unique sequence heavy chains and thirty unique sequence light chains were used for evaluation of expression levels. In all experiments plasmid DNA was carefully quantified and used in transient transfection to produce full human IgG protein, which was then quantified by ELISA. First, a single functional heavy chain was paired with each of the 30 light chains. In parallel a single light chain was paired with each of the 30 functional heavy chains. This allowed the selection of the top 16 expressing heavy chains and top 16 light chains to generate four 8×8 matrices. An example matrix is shown in FIG. 9.

Figure 10:
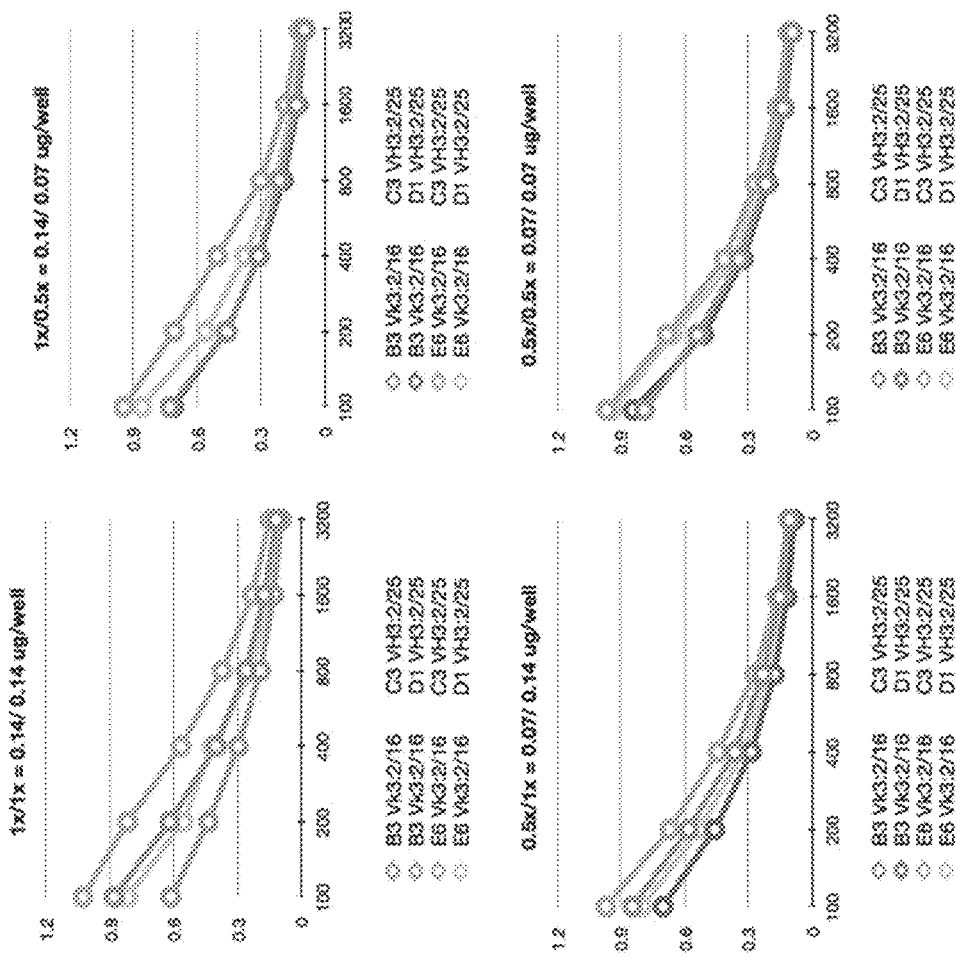
FIG. 10 are graphs showing the stability of various antibodies after an extended incubation period.

The top 2 heavy and light chains were selected from these matrices and were further analyzed in transient transfection by varying the plasmid DNA concentrations. Also, the relative stability of the different pairs was evaluated by extended incubation at 37° C. prior to protein quantification. The results of these experiments shown in FIG. 10 clearly demonstrate that the optimal pair for expression level and stability is clone "E6" light chain and clone "C3" heavy chain. The framework regions of these V genes were therefore used as the basis for the construction of the SynV light chain and heavy chain loci, respectively. The nucleotide sequences of the E6 and C3 clones and the encoded amino acid sequences are shown in FIGS. 11 and 12.

What is claimed is:

1. A transgenic chicken that comprises a genome comprising a recombinant immunoglobulin light chain (IgL) locus comprising:
   (a) a functional IgL gene comprising a nucleic acid encoding a light chain variable region comprising:
      (i) light chain complementarity determining (CDR) regions; and
      (ii) a light chain framework; and,
   (b) a plurality of pseudogenes that encode light chain variable regions each comprising:
      (i) light chain CDR regions; and
      (ii) a light chain framework region that is identical in amino acid sequence to the light chain framework of a) (ii);
   wherein said nucleic acid of (a) and pseudogenes of (b), are exogenous to the genome of said transgenic chicken, wherein said plurality of pseudogenes are operably linked to said functional IgL gene and donate nucleotide sequences to the nucleic acid of (a) by gene conversion in said transgenic chicken; and wherein said transgenic chicken expresses a polyclonal serum comprising a diversified IgL variable region.

2. The transgenic chicken of claim 1, wherein said light chain framework is identical to a human framework.

3. The transgenic chicken of claim 1, wherein said light chain framework is at least 95% identical to a human germline framework.

4. The transgenic chicken of claim 1, wherein said light chain framework is from the chicken.

5. The transgenic chicken of claim 1, wherein said light chain framework is a humanized framework.

6. The transgenic chicken of claim 1, wherein the constant region is a chicken constant region.

7. The transgenic chicken of claim 1, wherein said immunoglobulin light chain locus comprises at least 10 of said pseudogenes.

8. The transgenic chicken of claim 1, wherein at least one of said plurality of pseudogenes of b) is in an opposite orientation relative to the nucleic acid of a).

9. A method comprising:
(A) immunizing a transgenic chicken of claim 1 with an antigen, and
(B) obtaining from said transgenic chicken an antibody that specifically binds to said antigen, or a B cell that produces the same.

10. The method of claim 9, further comprising:
making hybridomas using cells of said transgenic chicken; and
screening said hybridomas to identify a hybridoma that produces an antibody that specifically binds to said antigen.

11. The method of claim 9, further comprising amplifying the heavy and light chain variable region-encoding nucleic acid from lymphocytes of said transgenic chicken, introducing the amplified nucleic acid into a cell and expressing the nucleic acid in said cell, thereby producing a recombinant antibody comprising the heavy and light chain variable regions of the antibody.

12. The method of claim 9, wherein the antibody is humanized.

13. An isolated B cell of the transgenic chicken of claim 1, wherein the B cell secretes an antibody.

14. The isolated B cell of claim 13, wherein the antibody is post-translationally modified by the B cell.

15. The isolated B cell of claim 14, wherein the antibody is glycosylated by the B cell.

* * * * *